(12) United States Patent
Broly et al.

(10) Patent No.: US 7,842,292 B2
(45) Date of Patent: Nov. 30, 2010

(54) METHODS FOR TREATING B-CELL MALIGNANCIES USING A TACI-IG FUSION MOLECULE

(75) Inventors: Herve Broly, Saint Selve (FR); Arnaud Ythier, Collex-Bossy (CH); Eric Sievers, Seattle, WA (US); Sharon J. Busby, Seattle, WA (US); Jan Öhrström, Mercer Island, WA (US); Ivan Nestorov, Issaquah, WA (US); Stephen M. Ansell, Rochester, MN (US)

(73) Assignees: Ares Trading S.A. (CH); Zymogenetics, Inc., Seattle, WA (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 11/502,134

(22) Filed: Aug. 9, 2006

(65) Prior Publication Data

US 2007/0071760 A1 Mar. 29, 2007

Related U.S. Application Data

(60) Provisional application No. 60/706,912, filed on Aug. 9, 2005.

(51) Int. Cl.
*A61K 39/395* (2006.01)
(52) U.S. Cl. .................................. 424/133.1; 424/155.1
(58) Field of Classification Search .............. 424/133.1, 424/155.1
See application file for complete search history.

(56) References Cited

U.S. PATENT DOCUMENTS

| | | | |
|---|---|---|---|
| 4,331,647 A | 5/1982 | Goldenberg |
| 4,486,533 A | 12/1984 | Lambowitz |
| 4,579,821 A | 4/1986 | Palmiter et al. |
| 4,599,311 A | 7/1986 | Kawasaki |
| 4,601,978 A | 7/1986 | Karin |
| 4,615,974 A | 10/1986 | Kingsman et al. |
| 4,656,134 A | 4/1987 | Ringold |
| 4,661,454 A | 4/1987 | Botstein et al. |
| 4,713,339 A | 12/1987 | Levinson et al. |
| 4,784,950 A | 11/1988 | Hagen et al. |
| 4,845,075 A | 7/1989 | Murray et al. |
| 4,870,008 A | 9/1989 | Brake |
| 4,882,279 A | 11/1989 | Cregg |
| 4,931,373 A | 6/1990 | Kawasaki et al. |
| 4,935,349 A | 6/1990 | McKnight et al. |
| 4,946,778 A | 8/1990 | Ladner et al. |
| 4,956,288 A | 9/1990 | Barsoum |
| 4,977,092 A | 12/1990 | Bitter |
| 4,990,446 A | 2/1991 | Oberto et al. |
| 5,037,743 A | 8/1991 | Welch et al. |
| 5,063,154 A | 11/1991 | Fink et al. |
| 5,139,936 A | 8/1992 | Botstein et al. |
| 5,143,830 A | 9/1992 | Holland et al. |
| 5,155,027 A | 10/1992 | Sledziewski et al. |
| 5,162,222 A | 11/1992 | Guarino et al. |
| 5,162,228 A | 11/1992 | Sumino et al. |
| 5,208,146 A | 5/1993 | Irie |
| 5,223,409 A | 6/1993 | Ladner et al. |
| 5,403,484 A | 4/1995 | Ladner et al. |
| 5,523,227 A | 6/1996 | Bram et al. |
| 5,541,291 A | 7/1996 | Keene |
| 5,567,584 A | 10/1996 | Sledziewski et al. |
| 5,571,698 A | 11/1996 | Ladner et al. |
| 5,595,721 A | 1/1997 | Kaminski et al. |
| 5,637,677 A | 6/1997 | Greene et al. |
| 5,650,550 A | 7/1997 | Korach et al. |
| 5,693,762 A | 12/1997 | Queen et al. |
| 5,716,808 A | 2/1998 | Raymond |
| 5,736,383 A | 4/1998 | Raymond |
| 5,739,277 A | 4/1998 | Presta et al. |
| 5,969,102 A | 10/1999 | Bram et al. |
| 6,015,801 A | 1/2000 | Daifotis et al. |
| 6,316,222 B1 | 11/2001 | Bram et al. |
| 6,500,428 B1 | 12/2002 | Bram et al. |
| 6,537,540 B1 | 3/2003 | Burstein et al. |
| 6,716,576 B1 | 4/2004 | Yu et al. |
| 6,774,106 B2 | 8/2004 | Theill et al. |
| 7,501,487 B1 | 3/2009 | Mangelsdorf et al. |
| 2003/0022233 A1 | 1/2003 | Goodwin et al. |
| 2003/0103986 A1 | 6/2003 | Rixon et al. |
| 2004/0013674 A1 | 1/2004 | Ambrose et al. |

(Continued)

FOREIGN PATENT DOCUMENTS

AU 2006201471 5/2006

(Continued)

OTHER PUBLICATIONS

Martino, FierceBiotech, Press Release: ZymoGenetics and Serono to Begin TACI-Ig Clinical Studies in B-cell Malignancies, pp. 1-4, Nov. 9, 2006.*

(Continued)

*Primary Examiner*—Lynn Bristol
(74) *Attorney, Agent, or Firm*—Howrey LLP

(57) ABSTRACT

The present invention provides methods and compositions for treatment of B-cell malignancies, including non-Hodgkin's lymphoma, comprising administering to a patient in need of the treatment a TACI-Ig fusion molecule in amount sufficient to suppress proliferation-inducing functions of BlyS and APRIL.

19 Claims, 4 Drawing Sheets

U.S. PATENT DOCUMENTS

| | | | |
|---|---|---|---|
| 2005/0070689 A1 | 3/2005 | Dixit et al. | |
| 2005/0163775 A1 | 7/2005 | Chan et al. | |
| 2005/0183148 A1 | 8/2005 | Bram et al. | |
| 2006/0034852 A1* | 2/2006 | Rixon et al. | 424/155.1 |
| 2006/0067933 A1 | 3/2006 | Gross et al. | |
| 2006/0073146 A1* | 4/2006 | Ashkenazi et al. | 424/144.1 |
| 2006/0286093 A1 | 12/2006 | Gross et al. | |
| 2007/0071760 A1 | 3/2007 | Broly et al. | |
| 2007/0264689 A1 | 11/2007 | Gross et al. | |
| 2007/0269443 A1 | 11/2007 | Kalled et al. | |

FOREIGN PATENT DOCUMENTS

| | | |
|---|---|---|
| EP | 0869180 A1 | 10/1998 |
| EP | 1666052 A | 6/2006 |
| GB | 9828628.9 | 12/1998 |
| WO | WO 91/11465 | 8/1991 |
| WO | WO 94/06463 | 3/1994 |
| WO | WO 94/09137 | 4/1994 |
| WO | WO 95/35501 | 12/1995 |
| WO | WO 96/18641 | 6/1996 |
| WO | WO 96/27011 | 9/1996 |
| WO | WO 97/09137 | 3/1997 |
| WO | WO 97/17450 | 5/1997 |
| WO | WO 97/17451 | 5/1997 |
| WO | WO 97/33902 | 9/1997 |
| WO | WO 98/02536 | 1/1998 |
| WO | WO 98/02565 | 1/1998 |
| WO | WO 98/18921 | 5/1998 |
| WO | WO 98/27114 | 6/1998 |
| WO | WO 98/39361 | 9/1998 |
| WO | WO 98/55620 | 12/1998 |
| WO | WO 98/55621 | 12/1998 |
| WO | WO 99/04001 | 1/1999 |
| WO | WO 99/11791 | 3/1999 |
| WO | WO 99/12964 | 3/1999 |
| WO | WO 99/12965 | 3/1999 |
| WO | WO 00/03995 | 1/2000 |
| WO | WO 00/39295 | 7/2000 |
| WO | WO 00/40714 A2 | 7/2000 |
| WO | WO 00/40716 | 7/2000 |
| WO | WO 00/43032 | 7/2000 |
| WO | WO 00/50597 | 8/2000 |
| WO | WO 00/62790 | 10/2000 |
| WO | WO 00/67034 | 11/2000 |
| WO | WO 01/12812 A2 | 2/2001 |
| WO | WO 01/24811 A1 | 4/2001 |
| WO | WO 01/60397 | 8/2001 |
| WO | WO 01/77342 | 10/2001 |
| WO | WO 01/81417 A2 | 11/2001 |
| WO | WO 01/87977 | 11/2001 |
| WO | PCT/JP01/06944 | 2/2002 |
| WO | WO 02/14504 | 2/2002 |
| WO | WO 02/38766 | 5/2002 |
| WO | WO 02/066516 | 8/2002 |
| WO | WO 02/094852 A2 | 11/2002 |
| WO | WO 03/001877 | 1/2003 |
| WO | WO 03/014294 | 2/2003 |
| WO | WO 03/055979 | 7/2003 |
| WO | WO 2005/005462 | 1/2005 |
| WO | WO 2005/042009 | 5/2005 |
| WO | WO 2006/052493 | 5/2006 |
| WO | WO 2006/068867 | 6/2006 |
| WO | WO 2007/019573 A2 | 2/2007 |
| WO | WO 2007/019575 A2 | 2/2007 |
| WO | WO 2007/019618 | 2/2007 |
| WO | WO 2007/134326 | 11/2007 |

OTHER PUBLICATIONS

Burgess et al, Journal of Cell Biology 111:2129-2138 (Nov. 1990).*
Lazar et al., Molecular and Cellular Biology 8(3) 1247-1252) (1988).*
Schwartz et al., Proc Natl Acad Sci USA 84:6408-6411 (1987).*
Lin et al Biochemistry USA 14:1559-1563 (1975).*
U.S. Appl. No. 09/627,206, filed Jul. 2000, Gross, Jane.*
Ibragimova and Eade (Biophysical Journal, Oct. 1999, vol. 77, pp. 2191-2198).*
Smith et al. (Nature Biotechnology 15:1222-1223 (1997)).*
Brenner (Trends in Genetics 15:132-133 (1999)).*
Lee (Arch Pharm Res. 25(5):572-84 (2002)).*
Ansell et al. (Clin. Cancer Res. 14(4):1105-1110 (Feb. 15, 2008)).*
Barlogie, B., et al. Extended Survival in Advanced and Refractory Multiple Myeloma After Single-Agent Thalidomide: Identification of Prognostic Factors in a Phase 2 Study of 169 Patients, Blood, vol. 98, No. 2, pp. 492-494 (2001).
Do, R., "Attenuation of Apoptosis Underlies B Lymphocyte Stimulator Enhancement of Humoral Immune Response." J. Exp. Med., vol. 192, No. 7, pp. 953-964 (2000).
Mackay, F., et al., "Mice Transgenic for BAFF Develop Lymphocytic Disorders Along with Autoimmune Manifestations," J. Exp. Med., vol. 190, No. 11, pp. 1697-1710 (1999).
Moore, P., et al., "BLyS: Member of the Tumor Necrosis Factor Family and B Lymphocyte Stimulator," Science, vol. 285, pp. 260-263 (1999).
Richardson, P., et al., "A Phase 2 Study of Bortezomib in Relapsed, Refractoroy Myeloma," N Engl J Med, vol. 348, No. 26, pp. 2609-2617 (2003).
Schneider, P., et al., "BAFF, A Novel Ligand of the Tumor Necrosis Factor Family, Stimulates B Cell Growth," J. Exp. Med., vol. 189, No. 11, pp. 1747-1756 (1999).
Cheema, G., et al., "Elevated Serum B Lmphocyte Stimulator Levels in Patients With Systemic Immune-Based Rheumatic Diseases," Arthritis & Rheumatism, vol. 44., No. 6, pp. 1313-1319 (2001).
Cheson, B., et al., "National Cancer Institute-Sponsored Working Group Guidelines for Chronic Lymphocytic Leukemia: Revised Guidelines for Diagnosis and Treatment," Blood, vol. 87, No. 12, pp. 4990-4997 (1996).
Groom, J., et al., "Association of BAFF/BLyS Overexpression and Altered B Cell Differentiation With Sjogren's Syndrome," The Journal of Clinical Investigation, vol. 109, No. 1, pp. 59-68 (2002).
Gross, J., et al., "TACI-Ig Neutralizes Molecules Critical for B Cell Development and Autoimmune Disease: Impaired B Cell Maturation in Mice Lacking BLyS," vol. 15, pp. 289-302 (2001).
Gross, J., et al., "TACI and BCMA are Receptors for a TNF Homologue Implicated in B-Cell Autoimmune Disease," Nature, vol. 404, pp. 995-999 (2000).
Hahne, M., et al., "APRIL, a New Ligand of the Tumor Necrosis Factor Family, Stimulates Tumor Cell Growth," Journal of Experimental Medicine, vol. 188, No. 6, pp. 1185-1190 (1998).
Kelly, K, "APRIL/TRDL-1, a Tumor Necrosis Factor-Like Ligand, Stimulates Cell Death," Cancer Research, vol. 60, pp. 1021-1027 (2000).
Marlette, X., et al., "The Level of BLyS (BAFF) Correlates with the Titre of Autoantibodies in Human Sjogren's Syndrome," Annals of the Rheumatic Diseases, vol. 62, pp. 168-171 (2003).
Marsters, S., et al., "Interaction of the TNF Homologues BLyS and APRIL with the TNF Receptor Homologues BCMA and TACI," Current Biology, vol. 10, pp. 785-788 (2000).
Roschke, V., et al., "BLyS and APRIL Form Biologically Active Heterotrimers That Are Expressed in Patients with Systemic Immune-Based Rheumatic Diseases," Journal of Immunology, vol. 169, pp. 4314-4321 (2002).
Thompson, J., et al., "BAFF-R, a Newly Identified TNF Receptor That Specifically Interacts with BAFF," Science, vol. 293, pp. 2108-2111 (2001).
Davidson and Diamond, "Autoimmune Diseases," N Engl J Med, vol. 345, No. 5, pp. 340-350 (Aug. 2, 2001).

DiLillo, D.J., et al., "Maintenance of Long-Lived Plasma Cells and Serological Memory Despite Mature and Memory B Cell Depletion during CD20 Immunotherapy in Mice," The Journal of Immunology, vol. 180, pp. 361-371 (2008).

Ding and Jones, "Belimumab Human Genome Sciences/Cambridge Antibody Technology," Current Opinion in Investigational Drugs, vol. 7, No. 5, pp. 464-472 (2006).

Durfee, T., et al., Genes Dev., vol. 7, pp. 555-569 (1993).

Dynan, T., Nature, vol. 316, pp. 774-778 (1985).

Eisen, "Aberrant Immune Responses," General Immunology, J.B. Lippincott Company, pp. 215-225 (1990).

Emmel, E.A., et al., "Cyclosporin A Specifically Inhibits Function of Nuclear Proteins Involved in T Cell Activation," Science, vol. 246, pp. 1617-1620 (Dec. 22, 1989).

European Search Report of EP 05020384.3 dated Apr. 27, 2007.

European Search Report of EP 03016020 dated Jul. 10, 2003.

European Search Report of EP 05018984 dated Jan. 25, 2006.

European Search Report of EP 05018985 dated Jan. 16, 2006.

European Supplementary & Partial Search Report of EP 02734478 dated Dec. 7, 2007.

Excoffon, K., et al., "The Role of the Extracellular Domain in the Biology of the Coxsackievirus and Adenovirus Receptor," Am. J. Respir. Cell. Mol. Biol., vol. 32, pp. 498-503 (2005).

Falk, et al., "The Systemic Amyloidoses," N Engl J Med, vol. 337, No. 13, pp. 898-909 (Sep. 25, 1997).

Feldmann and Maini, "The Role of Cytokines in the Pathogenesis of Rheumatoid Arthritis," Rheumatology, vol. 38, Suppl. 2, pp. 3-7 (1999).

Feldmann, et al., "Evaluation of the Role of Cytokines in Autoimmune Disease: The Importance of TNFa in Rheumatoid Arthritis," Progress in Growth Factor Research, vol. 4, pp. 247-255 (1992).

Fiering, S., et al., "Single Cell Assay of a Transcription Factor Reveals a Threshold in Transcription Activated by Signals Emanating from the T-cell Antigen Receptor," Genes & Development, vol. 4, pp. 1823-1834 (1990).

Friedman, J. and I. Weissman, "Two Cytoplasmic Candidates for Immunophilin Action Are Revealed by Affinity for a New Cyclophilin: One in the Presence and One in the Absence of CsA," Cell, vol. 66, pp. 799-806 (Aug. 23, 1991).

Gao, X., et al., "Advanced Transgenic and Gene-Targeting Approaches," Neurochemical Research, vol. 24, No. 9, pp. 1181-1188 (1999).

Houdebine, "Transgenic Animal Bioreactors," Transgenic Research, vol. 9, pp. 305-320 (2000).

Houdebine, L-M., 2002, Journal of Biotechnology, vol. 98, p. 145-160.

Huard, et al., "BAFF Production by Antigen-Presenting Cells Provides T Cell Co-Stimulation," International Immunology, vol. 16, No. 3, pp. 467-475 (2004).

Huard, et al., "T Cell Costimulation by the TNF Ligand BAFF," Journal of Immunology, vol. 167, pp. 6225-6231 (2001).

Hubbard, M.J., et al., vol. 28, pp. 1868-1874 (1989).

Hymowitz, et al., "Structures of APRIL-Receptor Complexes," Journal of Biological Chemistry, vol. 280, No. 8, pp. 7218-7227 (2005).

Idemura, J. Mol Biol., vol. 158, pp. 573-597 (1982).

Imboden, J.B., et al., "The Antigen Receptor on a Human T Cell Line Initiates Activation by Increasing Cytoplasmic Free Calcium" Journal of Immunology, vol. 134, No. 2, pp. 663-665 (Feb. 1985).

Inbar, et al., Proc. Natl. Acad. Sci., vol. 69, p. 2659 (1972).

InNEXUS Lead Candidate DXL625Outpeforms Rituxan in Additional Animal Studies, [Online] Retrieved from Scientific Blogging, XP-002515036, (2008, pp. 1-2, Presentation American Association for Cancer Research, San Diego, CA, 2008, pp. 1-14.

Interlocutory Decision in Opposition Proceedings of EP 00902354 dated Nov. 30, 2007.

International Preliminary Report on Patentability of PCT/US00/00396 dated Jun. 19, 2001.

International Preliminary Report on Patentability of PCT/US2006/031277 dated Aug. 9, 2005.

International Preliminary Report on Patentability of PCT/US2007/068982 dated Nov. 27, 2008.

International Preliminary Report on Patentability of PCT/US98/04270 dated Jan. 5, 1999.

International Search Report for WO 99/12964 dated Apr. 13, 1999.

International Search Report of PCT/US00/00396 dated Jul. 7, 2000.

International Search Report of PCT/US2007/068982 dated Mar. 3, 2008.

International Search Report of PCT/US2008/080177 dated Feb. 26, 2009.

International Search Report of PCT/US98/04270 dated Aug. 21, 1998.

Jones, et al., Nature, vol. 321, p. 522 (1986).

Kalled, S.L., et al., "BAFF; B Cell Survival Factor and Emerging Therapeutic Target for Autoimmune Disorders," Expert Opin. Ther. Targets, vol. 7, No. 1, pp. 115-123 (2003).

Karttunen, J., and N. Shastri, "Measurement of Ligand-induced Activation in Single Viable T Cells Using the lacZ Reporter Gene," Proc. Natl. Acad. Sci. USA, vol. 88, pp. 3972-3976 (May 1991).

Ramakrishnan and Scheid, "Diagnosis and Management of Acute Pyelonephritis in Adults," American Family Physician, vol. 71, No. 5, pp. 933-942 (Mar. 1, 2005).

Ramanujam, M. et al., "Mechanism of Action of Transmembrane Activator and Calcium Modulator Ligand Interactor-Ig in Murine Systemic Lupus Erythematosus," J. Immunol., vol. 173, 3524-3534 (2004).

Ramser, et a I., GenBank Report for Accession No. AL353996 (2000).

Raymond, et al., Yeast, vol. 14, pp. 11-23 (1998).

Roitt, I., et al., "Autoimmunity and Autoimmune Disease—27," Immunolgy, Fourth Edition, pp. 271-272 (1996).

Rudinger, J., "Characteristics of the Amino Acids as Components of Peptide Hormone Sequence," Peptide Hormones, University Park Press, Baltimore, pp. 1-7, (Jun. 1976).

Ryan, M., et al., "Antibody Targeting of B-Cell Maturaiton Antigen on Malignant Plasma Cells," Molecular Cancer Therapeutics, vol. 16, No. 11, US American Associate of Cancer Research pp. 3009-3018 (Nov. 2007).

Santee, S.M., and L.B. Owen-Schaub, "HumanTumor Necrosis Factor Receptor p75/80 (CD120B) Gene Structure and Promoter Characterization," The Journal of Biological Chemistry, vol. 271, No. 35, pp. 21151-21159 (1996).

Scatchard Ann. Ny. Acad. Sci., vol. 51, p. 660 (1949).

Sethi, S., et al., "Oxidized Omega-3 Fatty Acids in Fish Oil Inhibit Leukocyte-Endothelial Interactions Through Activation of Pparg," Blood, vol. 100, No. 4, pp. 1340-1346 (2002).

Shu, et al., J. Leukoc Biol., vol. 65, pp. 680-683 (1999).

Sigmund, C., Jun. 2000, Arterioscler. Thromb. Vasc. Biol., p. 1425-1429.

Silverman, G.J., et al., "B Cell Modulation in Rheumatology," Current Opinion in Pharmacology—Cancer/Immunomodulation 200708 GB, vol. 7, No. 4, pp. 426-433 (Aug. 4, 2007).

Singer, et al., J. Immun., vol. 150, p. 2844 (1993).

Sinkar, et al., J. Biosci., vol. 11, pp. 47-58 (1987).

Sipos, L., et al., Eur. J. Biochem., vol. 213, pp. 1333-1340 (1993).

Smith, et al, "The TNF Receptor Superfamily of Cellular and Viral Proteins" Activation, Costimulation and Death vol. 76, pp. 959-962 (1994).

Smith, Johnson, Gene, vol. 67, p. 31 (1988).

Stein, et al., "Immunologic Markers in the Differential Diagnosis of Non-Hodgkins Lymphomas," Journal of Cancer Research and Clinical Oncology, vol. 101, p. 29, Abstract (1981).

Von Bulow, G. U. and R.J. Bram, "NF-AT Activation Induced by a CAML-Interacting Member of the Tumor Necrosis Factor Receptor Superfamily," Science, vol. 278, pp. 138-141 (Oct. 3, 1997).

Von Bulow and R.J. Bram, "Activation of the Transcription Factor NFAT by a Novel CAML-Interacting Member of the Tumor Necrosis Factor Receptor Superfamily," Blood, vol. 90, No. 10, Suppl. 1, Part 1, pp. 246A-247 (1997).

Von Bulow, G.U., et al., "Molecular Cloning and Functional Characterization of Murine Transmembrane Activator and CAML Interactor (TACI) with Chromosomal Localization in Human and Mouse," Mammalian Genome, vol. 11, pp. 628-632 (2000).

Vugmeyster, Y., et al., "A Soluble BAFF Antagonist, BR3-Fc, Decreases Peripheral Blood B Cells and Lymphoid Tissue Marginal Zone and Follicular B Cells in Cynomolgus Monkeys," American Journal of Pathology 200602 US, vol. 168, No. 2, pp. 476-489 (Feb. 2, 2006).

Wada, A., et al., "Identification of Ligand Recognition Sites in Heat-Stable Enterotoxin Receptor, Membrane-Associated Guanylyl Cyclase C by Site-Directed Mutational Analysis," Infection and Immunity, vol. 64, No. 12, pp. 5144-5150 (1996).

Wain-Hobson, et al., Gene, vol. 13, pp. 355-364 (1981).

Wallach, "TNF Ligand and TNF/NGF Receptor Families," Dept of Biological Chemistry, Weizmann Institute of Science, pp. 377-411 (2000).

Wang, et al., "TACI-Ligand Interactions are required for T Cell Activation and Collagen-Induced Arthritis in Mice," Nature Immunology, vol. 2, No. 7, pp. 632-637 (2001).

Ware, Nature, vol. 404, pp. 949-950 (2000).

Weiss, A., and D.R. Littman, et al., "Signal Transduction by Lymphocyte Antigen Receptors," Cell, vol. 76, pp. 263-274 (Jan. 28, 1994).

Wigler, et al., Cell, vol. 14, p. 7 25 (1978).

Wilson-Rawls, J., et al., Virology, vol. 201, pp. 66-76 (1994).

Wu, Y., et al., Tumor Necrosis Factor (TNF) Receptor Superfamily Member TACI is a High Affinity Receptor for TNF Family Members APRIL and BLyS, The Journal of Biological Chemistry, vol. 275, No. 45, pp. 35478-35485 (2000).

Xia et al., "TACI is a TRAF-Interacting Receptor for TALL-1, a Tumor Necrosis Factor Family Member Involved in B Cell Regulation," J. Exp. Med., vol. 192, No. 1, pp. 137-143 (Jul. 3, 2000).

Yan M., et al., "Activation and Accumulation of B Cells in TACI-Deficient Mice," Nat. Immunol., vol. 2, 638-643 (2001).

Yan, et al., Nature Immunol., vol. 1, pp. 37-41 (2000).

Yang, M., et al., "B Cell Maturation Antigen, the Receptor for a Proliferation-Inducing Ligand and B Cell-Activating Factor of the TNF Family, Induces Antigen Presentation in B Cells," Journal of Immunology, vol. 175, US The Williams and Wilkins Co., Baltimore, pp. 2814-2824 (Sep. 2005).

Yu, G., et al., "APRIL and TALL-I and Receptors BCMA and TACI: System for Regulating Humoral Immunity," Nature, vol. 1, No. 3, pp. 252-256 (2000).

Zhou, et al., Blood, vol. 98, No. 11:808a, Abstract 3361 (2001).

Zhu, J., et al., "Plasma Cells and IL-4 in Chronic Bronchitis and Chronic Obstructive Pulmonary Disease," American Journal of Respiratory and Critical Care Medicine, vol. 175, US American Lung Association, New York, NY vol. 175, pp. 1125-1133 (Jun. 2007).

Zweifach, A., and R.S. Lewis, "Mitogen-regulated $Ca^{2+}$ Current of T Lymphocytes is Activated by Depletion of Intracellular $Ca^{2+}$ Stores," Proc. Natl. Acad. Sci. USA, vol. 90, pp. 6295-6299 (Jul. 1993).

Berenbaum, "Synergy, Additivism and Antagonism in Immunosuppression," Clin. Exp. Immunol., vol. 28, pp. 1-18 (1977).

Bilsborough, J., et al., "TACI-Ig Prevents the Development of Airway Hyper-Responsiveness in a Murine Model of Asthma," Clinical & Experimental Allergy, vol. 38, No. 12, pp. 1959-1968 (2008).

Dooley, M., et al., "Mycophenolate Mofetil Therapy in Lupus Nephritis: Clinical Observations," J. Am. Soc. Nephrol., vol. 10, pp. 833-839 (1999).

Jonsson., et al., "Mycophenolic Acid Inhibits Inosine 5'-Monophosphate Dehydrogenase and Suppresses Immunoglobulin and Cytokine Production of B Cells," International Immunopharmacology, vol. 3, pp. 31-37 (2003).

Koyama, et al., "Raised Serum APRIL Levels in Patients with Systemic Lupus Erythematosus," Ann Rheum. Dis., vol. 64, pp. 1065-1067 (2005).

Pena-Rossi, C., et al., "An Exploratory Dose-Escalating Study Investigating the Safety, Tolerability, Pharmacokinetics and Pharmacodynamics of Intravenous Atacicept in Patients with Systemic Lupus Erythematosus," Lupus, vol. 18, No. 6, pp. 547-555 (2009).

Stohl, W., et al., "B Lymphocyte Stimulator Protein-Associated Increase in Circulating Autoantibody Levels May Require CD4+ T Cells: Lessons from HIV-Infected Patients," Clinical Immunology, vol. 104, Issue 3, pp. 115-122 (2002).

Tak, P. P., et al., "Atacicept in Patients with Rheumatoid Arthritis: A, Multi-Center, double-Blind, Placebo-Controlled, Dose-Escalating, Single and Repeat Dose Study," Arthritis Rheum., vol. 58, No. 1, pp. 61-72 (2008).

U.S. Appl. No. 09/569,245 Final office action dated Nov. 17, 2009.
U.S. Appl. No. 09/627,206 Final office action dated Oct. 27, 2009.
U.S. Appl. No. 11/501,999 Non-final office action dated Dec. 4, 2009.
U.S. Appl. No. 11/748,978 Non-final office action dated Dec. 4, 2009.
U.S. Appl. No. 11/458,968 Notice of Allowance dated Dec. 16, 2009.
U.S. Appl. No. 12/057,133 Non-Final Office Action dated Feb. 4, 2010.

Moon and Ryu, "TACI: Fc Scavenging B Cell Activating Factor (BAFF) Alleviates Ovalbumin-Induced Bronchial Asthma in Mice," Exp. Mol. Med., vol. 39, No. 3, pp. 343-352 (Jun. 2007).

Mukhopadhyay, et al., "Identification and Characterization of a Novel Cytokine, THANK, a TNF Homologue That Activates Apoptosis, Nuclear Factor-kB, and c-Jun NH2-Terminal Kinase," Journal of Biological Chemistry, vol. 274, No. 23, pp. 15978-15981 (1999).

Munafo, et al., "Safety, Pharmacokinetics and Pharmacodynamics of Atacicept in Healthy Volunteers," Eur J Clin Pharmacol, vol. 63, pp. 647-656 (Apr. 2, 2007).

Neumann, et al., Embo J., vol. 1, pp. 841-845 (1982).

Ng, et al., "B Cell-Activating Factor Belonging to the TNF Family (BAFF)-R Is the Principal BAFF Receptor Facilitating BAFF Costimulation of Circulating T and B Cells," Journal of Immunology, vol. 173, pp. 807-817 (2004).

Nilsson, et al., Embo J., vol. 4, p. 1075, (1985).
Nilsson, et al., Methods Enzymol., vol. 198, p. 3 (1991).
Nisonoff, et al., Biochem. Biophys, vol. 89, p. 230 (1960).
Novake, Anne, J., et al., Blood, vol. 103, No. 2, pp. 689-694 (2004).

O'Keefe, S.J., et al., "FK-506 and CsA-sensitive Activation of the Interleukin-2 Promoter by Calcineurin," Nature, vol. 357, pp. 692-694 (Jun. 25, 1992).

Orlandi, et al., Proc. Natl. Acad. Sci., vol. 86, p. 3833 (1989).
Pack, et al., Bio/Technology, vol. 11, p. 1271 (1993).
Palacios, Steinemetz, Cell, vol. 41, pp. 727-734 (1985).

Panayi, "The Pathogenesis of Rheumatoid Arthritis: From Molecules to the Whole Patient," British Journal of Rheumatology, vol. 32, pp. 533-536 (1993).

Patel, et al., "Engineering an APRIL-specific B Cell Maturation Antigen," Journal of Biological Chemistry, vol. 279, No. 16, pp. 16727-16735 (Apr. 16, 2004).

Pena-Rossi, C., et al., "An Exploratory Dose-Escalating Study Investigating the Safety, Tolerability, Pharmacokinetics and Pharmacodynamics of Intravenous Atacicept in Patients with Systemic Lupus Erythematosus," Lupus 18(6) 547-55 (2009).

Perez-Melgosa, et al., J. Immunol., vol. 163, p. 1123-27 (1999).
Porter, Biochem. J., vol. 73, p. 119 (1959).

Premack, B.A., et al., "Activation of $CA^{2+}$ Current in Jurkat T Cells Following the Depletion of $Ca^{2+}$ Stores by Microsomal $Ca^{2+}$-ATPase Inhibitors," Journal of Immunology, vol. 152, pp. 5226-5240 (1994).

Putney, J.W., Jr., and G.St. J. Bird, The Signal for Capactiative Calcium Entry, Cell, vol. 75, pp. 199-201 (Oct. 22, 1993).

Biosis Database, [online], Biosciences Information Service, Philadelphia, PA (Sep. 2008). Carbonatto, Michela, et al., Nonclinical Safety, Pharmacokinetics, and Pharmacodynamics of Atacicept, Database Accession No. PRV200800586339, Toxicological Sciences, vol. 105, No. 1, pp. 200-210 (Sep. 2008).

Bird, et al., Science, vol. 242, p. 423 (1988).

Birren, et al., EMBL Database Report for Accession No. AC003958, Jan. 6, 1998 (XP-002072294).

Bodmer, et al., "The Molecular Architecture of the TNF Superfamily," Trends in Biochemical Sciences, vol. 27, No. 1, pp. 19-24 (Jan. 2002).

Bonning, et al., J. Gen. Virol., vol. 75, pp. 1551-1556 (1994).

Bram, R.J. and G.R. Crabtree, "Calcium Signalling in T Cells Stimulated by a Cyclophilin B-Binding Protein," Nature, vol. 371, pp. 355-358 (Sep. 22, 1994).

Bram, R.J., et al., "Identification of the Immunophilins Capable of Mediating Inhibition of Signal Transduction by Cyclosporin A and FK506: Roles of Calcineurin Binding and Cellular Location," Molecular and Cellular Biology, vol. 13, No. 8, pp. 4760-4769 (Aug. 1993).
Carter, et al., Proc. Nat. Acad. Sci., vol. 89, p. 42875 (1992).
Chan, A., et al., "Rescue Therapy Anti-CD20 Treatment in Neuroimmunologic Breakthrough Disease," J. Neurol. vol. 254, pp. 1604-1606 (2007).
Chazenbalk, Rapport, J. Biol. Chem., vol. 270, pp. 1543-1549 (1995).
Chirgwin, et al., Biochemistry, vol. 18, pp. 52-94 (1979).
Ciccarone, et al., Focus, vol. 15, p. 80 (1993).
Claros, M.G., et al., Comput. Appl. Biosci., vol. 10, pp. 685-686 (1994).
Clipstone, N.A. and G.R. Crabtee, "Identification of Calcineurin as a Key Signalling Enzyme in T-lymphocyte Activation," Nature, vol. 357, pp. 695-697 (Jun. 25, 1992).
Corsaro, Pearson Somatic Cell Genetics, vol. 7, p. 603 (1981).
Cosman, Stem Cells, vol. 12, pp. 440-455 (1994).
Courtenay-Luck, et al., "Genetic Manipulation of Monoclonal Antibodies, Cambridge University Press article," Monoclonal Antibodies, Production, Engineering and Clinical Application, p. 166 (1995).
Crabtee and Clipstone, Annu. Rev. Biochem., vol. 63, pp. 1045-1083 (1994).
Cyster, Nature Immunol., vol. 1, pp. 9-10 (2000).
Dall'Era, M., et al., Atacicept Reduces B Lymphocytes and Immunoglobulin Levels in Patients with Sytsemic Lupus Erythematosus (SLE) Arth. Rheum 56:4142-50 (2007).
Database Accession No. 014836, "Tumor Necrosis Factor Receptor Superfamily Member 13B" (2007).
Database Accession No. P20333, "Tumor Necrosis Factor Receptor 2 Precursor," (1995).
International Search Report of PCT/US2006/031277, dated Apr. 30, 2007.
International Search Report of PCT/US2006/031274, dated Apr. 30, 2007.
Anonymous, "Waldenstrom Macroglobulinemia," Wikipedia, The Free Encyclopedia, http://en.wikipedia.org/wiki/Waldenstrom_macroglobulinemia, (Apr. 14, 2008).
Stohl, et al., "B Cell Depletion Therapy in Systemic Rheumatic Diseases: Different Strokes for Different Folks?" Clinical Immunology, vol. 121, No. 1, pp. 1-12 (Oct. 1, 2006) (Abstract).
Strand V. et al., "Biologic Therapies in Rheumatology: Lessons Learned, Future Directions," Nat. Rev. Drug. Discov., vol. 6, No. 1, 75-92 (2007).
Stryer, L., "Flow of Genetic Information," Biochemistry Fourth Edicition, W.H. Freeman and Company, New York, pp. 111 (1996).
Stuve, O., et al., "Clinical Stabilization and Effective B-lymphocyte Depletion in the Cerebrospinal Fluid and Peripheral Blood of a Patient with Fulminant Relapsing-Remitting Multiple Sclerosis," Archives of Neurology, vol. 62, No. 10, pp. 1620-1623 (Oct. 2005).
Sulkowski, Trends in Biochem, vol. 1, p. 7 (1985).
Suntharalingam G., et al., "Cytokine Storm in a Phase 1 Trial of the Anti-CD28 Monoclonal Antibody TGN1412," N. Engl. J. Med., vol. 355, 1018-1028 (2006).
Tak, P. P., et al., "Atacicept in Patients with Rheumatoid Arthirits: A, Multi-Center, double-Blind, Placebo-Controlled, Dose-Escalating, Single and Repeat Dose Study," Arthritist Rheum 58: 61-72 (2008).
Takashi, et al., Japanese Journal of Science, vol. 28, No. 5, pp. 333-342, (Oct. 2005) Abstract.
Takebe, Y., et al., SráPromoter: an Efficient and Versatile Mammalian cDNA Expression System Composed of the Simian Virus 40 Early Prometer and the R-US Segment of Human T-Cell Leukemia Virus Type 1 Long Terminal Repeat, Molecular and Cellular Biology, vol. 8, No. pp. 466-472 (Jun. 1988).
Tashiro, K., et al., "Signal Sequence Trap: A Cloning Strategy for Secreted Proteins and Type I Membrane Proteins," Science, vol. 261, pp. 600-603 (Jul. 30, 1993).
Taylor, et al., Int. Immun., vol. 6, p. 579 (1994).
Thompson, et al., "BAFF Binds to the Tumor Necrosis Factor Receptor-like Molecule B Cell Maturation Antigen and is Important for Maintaining the Peripheral B Cell Population," J. Exp. Med., vol. 192, No. 1, pp. 129-135 (Jul. 3, 2000).
Truneh, A., et al., Early Steps of Lymphocyte Activation Bypassed by Synergy Between Calcium Ionophores and Phorbol Ester, Nature, vol. 313, pp. 318-320 (Jan. 24, 1985).
Tsokos, "Lymphocytes, Cytokines, Inflammation, and Immune Trafficking," Current Opinion in Rheumatology, vol. 7, pp. 376-383 (1995).
Tuan, et al., Connect Tiss. Res., vol. 34, pp. 1-9 (1996).
Varthakavi, Minocha, J. Gen. Virol., vol. 77, p. 1875 (1996).
Verweij, C.L., et al., "Cell Type Specificity and Activation Requirements for NFAT-1 (Nuclear Factor of Activated T-cells) Transcriptional Activity Determined by a New Method Using Transgenic Mice to Assay Transcriptional Activity of an Individual Nuclear Factor," Journal of Biological Chemistry, vol. 265, No. 26, pp. 15788-15795 (Sep. 15, 1990).
Khare, et al., Proc. Natl. Acad. Sci. USA, vol. 97, pp. 3370-3375 (2000).
Kohler, et al., Nature, vol. 257, p. 495 (1975).
Kolb, et al., Insertion of a Foreign Gene into the Beta-casein Locus by Cre-mediated Site-specific Recombination, Gene, vol. 227, pp. 21-31 (1999).
Korganow, et al., Immunity, vol. 10, pp. 451-461 (1999).
Kyte, Doolittle, J. Mol. Biol., vol. 157, pp. 105-142 (1982).
Laabi, et al., "A New Gene, BCM, on Chromosome 16 is Fused to the Interleukin 2 Gene by a t(4;16) (q26;p13) Translocation in a Malignant T Cell Lymphoma," EMBO Journal, vol. 11, No. 11, pp. 3897-3904 (1992).
Laabi, et al., "The BCMA Gene, Preferentially Expressed During B Lymphoid Maturation, is Bidirectionally Transcribed," Nucleic Acids Research, vol. 22, No. 7, pp. 1147-1154 (1994).
Larrick, et al., Methods: A Companion to Methods in Enzymology, vol. 2, p. 106 (1991).
Leiter, E.H. & Lee, C-H., "Is There Evidence for Genetic Overlap Between Type 1 and Type 2 Diabestes?" Diabetes, vol. 54, Supp. 2, pp. S151-S158 (2005).
Leiter, et al. "Mice with targeted gene disruptions or gene insertions for diabetes research; problems, pitfalls, and potential solutions," Diabetologia, vol. 45, pp. 296-308 (2002).
Liapakis, G., et al., "Identification of Ligand Binding Determinants in the Somatostatin Receptor Subtypes 2 and 2," Journal of Biological Chemnistry, vol. 271, No. 34, pp. 20331-20339 (1996).
Lin, J.C., et al., "A Microdomain Formed by the Extracellular Ends of the Transmembrane Domains Promotes Activation of the G Protein-Coupled ά-Factor Receptor," Molecular and Cellular Biology, vol. 24, No. 5, pp. 2041-2051 (2004).
Liu, J., et al., "Calcineurin is a Common Target of Cyclophilin-Cyclosporin A FKBP-FK506 Complexes," Cell, vol. 66, pp. 807-815 (Aug. 13, 1991).
Lonberg, et al., Nature, vol. 368, p. 856 (1994).
Losman, et al., Int. J. Cancer, vol. 46, p. 310 (1990).
Luckow, et al., J. Virol., vol. 67, pp. 4566-4579 (1993).
Madry, "The Characterization of Murine BCMA Gene Defines it as a New Member of the Tumor Necrosis Factor Receptor Superfamily," International Immunology, vol. 10, No. 11, pp. 1693-1702 (Aug. 3, 1998).
Mathey-Prevot, et al., Mol. Cell. Biol., vol. 6, pp. 4133-4135 (1986).
Merck, 17th Edition, Section 6-Pulmonary Disorders, pp. 568-569, (Mar. 1999).
Miller, et al., GenBank Report for Accession No. R24371, Apr. 20, 1995.
Mishra, GenBank Report for Accession No. V64412, Mar. 1, 1999.
Gamier, et al., Cytotechnol., vol. 15, pp. 145-155 (1994).
Ginzler, et al., "Safety Pharmacokinetic and Pharmacodynamic Results of a Phase 1 Single and Double Dose-Escalation Study of LymphoStat-B (Human Monoclonal Antibody to BLyS) in SLE Patients," American College of Rheumatology Abstract Supplement, pp. S377, (2003).
Gleeson, et al., J. Gen. Microbiol., vol. 132, pp. 3459-3465 (1986).
Graham, et al., J. Gen. Viol., vol. 36, pp. 59-72 (1977).
Graham, Van der Eb, Virology, vol. 52, p. 456 (1973).
Grantham, et al., Nuc.Acids Res., vol. 8, pp. 1893-1912 (1980).
Gras, et al., "BCMAp: An Integral Membrane Protein in the Golgi Apparatus of Human Mature B Lymphocytes," International Immunology, vol. 7, No. 7, pp. 1093-1106 (Mar. 28, 1995).

Green, et al., Nat. Genet, vol. 7, p. 13 (1994).
Grosjean, Fiers, Gene, vol. 18, pp. 199-209 (1982).
Grussenmeyer, et al., Proc. Natl. Acad. Sci., vol. 82, pp. 7952-7954 (1985).
Haas, et al., Cur. Biol., vol. 6, pp. 315-324 (1996).
Halpern et al., "Chronic Administration of Belimumab, a BLyS Antagonist, Decreases Tissue and Peripheral Blood B-Lymphocyte Populations in Cynomolgus Monkeys: Pharmacokinetic, Pharmacodynamic, and Toxicologic Effects," Toxicological Sciences, vol. 91, No. 2, pp. 586-599 (2006).
Hatzoglou, et al., J. Immunol., vol. 165, pp. 1322-1330 (2000) (XP002324045).
Hawley-Nelson, et al., Focus, vol. 15, p. 73 (1993).
Herrscher, R.F., et al., "The Immunoglobulin Heavy-chain Matrix-Associating Regions are Bound by Bright ά B Cell-Specific Trans-Activator That Describes A New DNA-Binding Protein Family," Genes & Development, vol. 9, pp. 30607-3082 (1995).
Hillier, et al., GenBank Report for Accession No. H47097, Aug. 16, 1995.
Hill-Perkins, Possee, J. Gen Virol., vol. 71, pp. 971-976 (1990).
Holloway, M.P. and R.J. Bram, "A Hydrophobic Domain of $Ca^{2+}$ Modulating Cyclophilin Ligand Modulates Calcium Influx Signaling in T Lymphocytes," The Journal of Biological Chemistry, vol. 271, No. 15, pp. 8549-8552 (1996).

Holloway, M.P. and R.J.Bram, "Co-localization of Calcium-modulating Cyclophilin Ligand with Intracellular Calcium Pools," Journal of Biological Chemistry, vol. 273, No. 26, pp. 16346-16350 (Jun. 26, 1992).
Holm, Nuc. Acids Res., vol. 14, pp. 3075-3087 (1986).
Hopp, Woods Proc. Nat. Acad. Sci., vol. 78, pp. 3824-3828 (1981).
Hoth, M. and R. Penner, Calcium Release-Activated Calcium Current in Rat Mast Cells, Journal of Physiology, vol. 465, pp. 359-386 (1993).
Altschul, et al., Bull Math. Bio., vol. 48, pp. 603-666 (1986).
Anolik, J.H., et al., "New Treatments for SLE: Cell-Depleting and Anti-Cytokine Therapies," Best Practice & Research Clinical Rheumatology, vol. 19, No. 5, pp. 859-878 (2005).
Aviv, H., et al., "Purificaton of Biologically Active Globin Messenger RNA by Chromatography on Oligothymidylic acid Cellulose," Proc. Natl. Acad. Sci., vol. 69, pp. 1408-1412 (1972).
Bairoch, A., "The PROSITE Dictionary of Sites and Patterns in Proteins, Its Current Status," Nucleic Acids Research, vol. 21, No. 13, pp. 3097-3103 (1993).
Bell, E., "TNF-R Homologues in Autoimmune Disease," Immunology Today, vol. 21, No. 6, p. 253 (Jun. 1, 2000).
Bilsborough, J., et al., "TACI-Ig Prevents the Development of Airway Hyper-Responsiveness in a Murine Model of Asthma," Clin. Exp. Allergy 38(12):1959-68 (2008).

* cited by examiner

Figure1: Dose Escalation Scheme
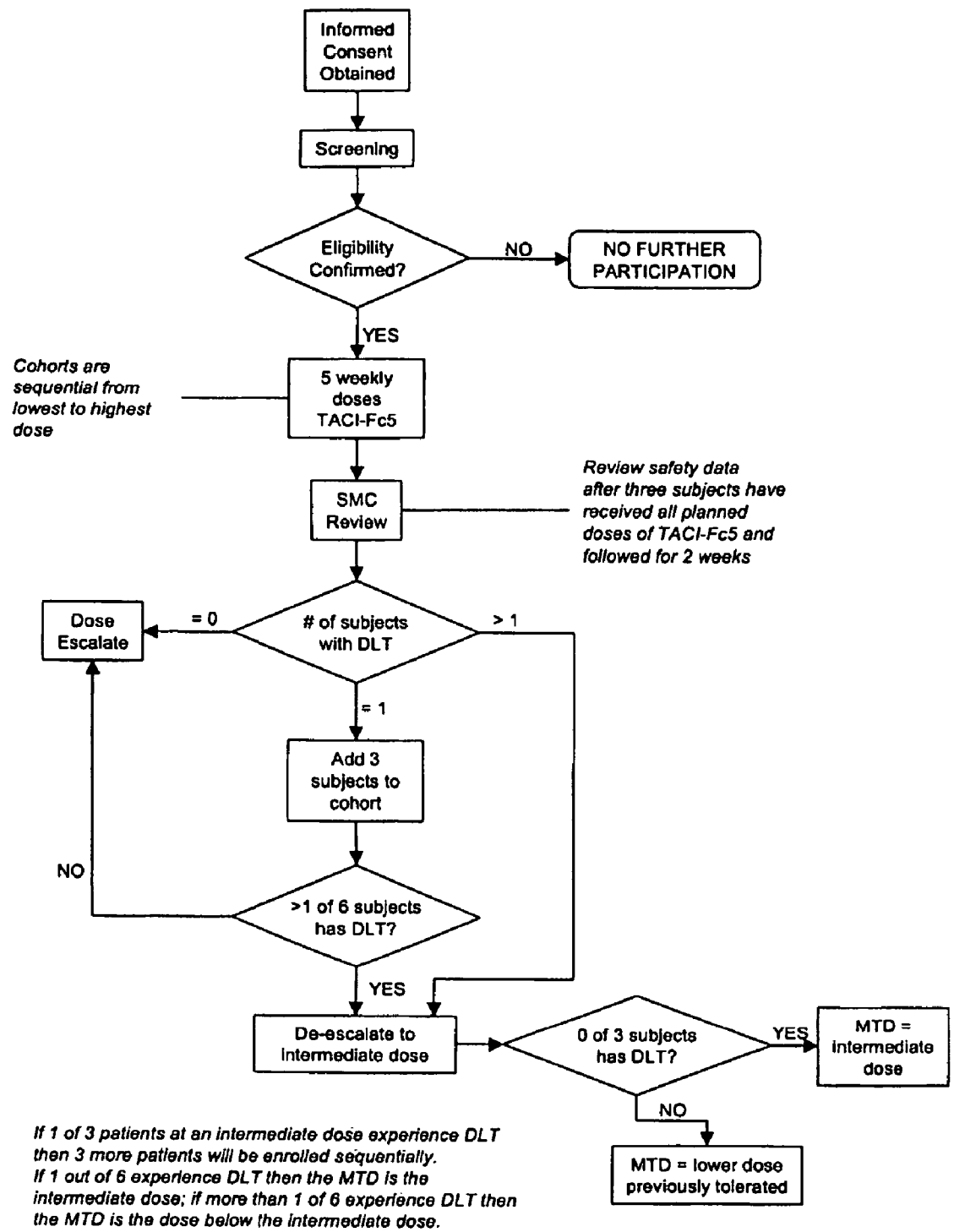

Figure 2. Areas for subcutaneous injection of TACI-Ig molecule.

Figure 3. SEQ ID NO. 1

```
Met Ser Gly Leu Gly Arg Ser Arg Arg Gly Gly Arg Ser Arg Val Asp
 1           5                   10                  15
Gln Glu Glu Arg Phe Pro Gln Gly Leu Trp Thr Gly Val Ala Met Arg
            20                  25                  30
Ser Cys Pro Glu Glu Gln Tyr Trp Asp Pro Leu Leu Gly Thr Cys Met
            35                  40                  45
Ser Cys Lys Thr Ile Cys Asn His Gln Ser Gln Arg Thr Cys Ala Ala
    50                  55                  60
Phe Cys Arg Ser Leu Ser Cys Arg Lys Glu Gln Gly Lys Phe Tyr Asp
65                  70                  75                  80
His Leu Leu Arg Asp Cys Ile Ser Cys Ala Ser Ile Cys Gly Gln His
                85                  90                  95
Pro Lys Gln Cys Ala Tyr Phe Cys Glu Asn Lys Leu Arg Ser Pro Val
            100                 105                 110
Asn Leu Pro Pro Glu Leu Arg Arg Gln Arg Ser Gly Glu Val Glu Asn
        115                 120                 125
Asn Ser Asp Asn Ser Gly Arg Tyr Gln Gly Leu Glu His Arg Gly Ser
    130                 135                 140
Glu Ala Ser Pro Ala Leu Pro Gly Leu Lys
145                 150
```

Figure 4. SEQ ID NO. 2

Met Asp Ala Met Lys Arg Gly Leu Cys Cys Val Leu Leu Leu Cys Gly
1               5                   10                  15
Ala Val Phe Val Ser Leu Ser Gln Glu Ile His Ala Glu Leu Arg Arg
            20                  25                  30
Phe Arg Arg Ala Met Arg Ser Cys Pro Glu Glu Gln Tyr Trp Asp Pro
            35                  40                  45
Leu Leu Gly Thr Cys Met Ser Cys Lys Thr Ile Cys Asn His Gln Ser
            50                  55                  60
Gln Arg Thr Cys Ala Ala Phe Cys Arg Ser Leu Ser Cys Arg Lys Glu
65                  70                  75                  80
Gln Gly Lys Phe Tyr Asp His Leu Leu Arg Asp Cys Ile Ser Cys Ala
                85                  90                  95
Ser Ile Cys Gly Gln His Pro Lys Gln Cys Ala Tyr Phe Cys Glu Asn
            100                 105                 110
Lys Leu Arg Ser Glu Pro Lys Ser Ser Asp Lys Thr His Thr Cys Pro
            115                 120                 125
Pro Cys Pro Ala Pro Glu Ala Glu Gly Ala Pro Ser Val Phe Leu Phe
    130                 135                 140
Pro Pro Lys Pro Lys Asp Thr Leu Met Ile Ser Arg Thr Pro Glu Val
145                 150                 155                 160
Thr Cys Val Val Val Asp Val Ser His Glu Asp Pro Glu Val Lys Phe
            165                 170                 175
Asn Trp Tyr Val Asp Gly Val Glu Val His Asn Ala Lys Thr Lys Pro
            180                 185                 190
Arg Glu Glu Gln Tyr Asn Ser Thr Tyr Arg Val Val Ser Val Leu Thr
            195                 200                 205
Val Leu His Gln Asp Trp Leu Asn Gly Lys Glu Tyr Lys Cys Lys Val
    210                 215                 220
Ser Asn Lys Ala Leu Pro Ser Ser Ile Glu Lys Thr Ile Ser Lys Ala
225                 230                 235                 240
Lys Gly Gln Pro Arg Glu Pro Gln Val Tyr Thr Leu Pro Pro Ser Arg
                245                 250                 255
Asp Glu Leu Thr Lys Asn Gln Val Ser Leu Thr Cys Leu Val Lys Gly
            260                 265                 270
Phe Tyr Pro Ser Asp Ile Ala Val Glu Trp Glu Ser Asn Gly Gln Pro
    275                 280                 285
Glu Asn Asn Tyr Lys Thr Thr Pro Pro Val Leu Asp Ser Asp Gly Ser
    290                 295                 300
Phe Phe Leu Tyr Ser Lys Leu Thr Val Asp Lys Ser Arg Trp Gln Gln
305                 310                 315                 320
Gly Asn Val Phe Ser Cys Ser Val Met His Glu Ala Leu His Asn His
                325                 330                 335
Tyr Thr Gln Lys Ser Leu Ser Leu Ser Pro Gly Lys
            340                 345

SEQUENCE LISTING

```
<160> NUMBER OF SEQ ID NOS: 2

<210> SEQ ID NO 1
<211> LENGTH: 154
<212> TYPE: PRT
<213> ORGANISM: Homo sapiens

<400> SEQUENCE: 1

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
        35                  40                  45

Ser Cys Lys Thr Ile Cys Asn His Gln Ser Gln Arg Thr Cys Ala Ala
    50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
        115                 120                 125

Asn Ser Asp Asn Ser Gly Arg Tyr Gln Gly Leu Gly His Arg Gly Ser
    130                 135                 140

Glu Ala Ser Pro Ala Leu Pro Gly Leu Lys
145                 150

<210> SEQ ID NO 2
<211> LENGTH: 348
<212> TYPE: PRT
<213> ORGANISM: Homo sapiens
```

```
<400> SEQUENCE: 2

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
            35                  40                  45

Leu Leu Gly Thr Cys Met Ser Cys Lys Thr Ile Cys Asn His Gln Ser
        50                  55                  60

Gln Arg Thr Cys Ala Ala Phe Cys Arg Ser Leu Ser Cys Arg Lys Glu
65                  70                  75                  80

Gln Gly Lys Phe Trp Asp His Leu Leu Arg Asp Cys Ile Ser Cys Ala
                85                  90                  95

Ser Ile Cys Gly Gln His Pro Lys Gln Cys Ala Tyr Phe Cys Glu Asn
                100                 105                 110

Lys Leu Arg Ser Glu Pro Lys Ser Ser Asp Lys Thr His Thr Cys Pro
            115                 120                 125

Pro Cys Pro Ala Pro Glu Ala Glu Gly Ala Pro Ser Val Phe Leu Phe
            130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
            195                 200                 205

Val Leu His Gln Asp Trp Leu Asn Gly Lys Glu Tyr Lys Cys Lys Val
        210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Ser Asn Gly Gln Pro
            275                 280                 285

Glu Asn Asn Tyr Lys Thr Thr Pro Pro Val Leu Asp Ser Asp Gly Ser
        290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

METHODS FOR TREATING B-CELL MALIGNANCIES USING A TACI-IG FUSION MOLECULE

CROSS-REFERENCE TO RELATED APPLICATIONS

This application claims the benefit of U.S. Provisional Application Ser. No. 60/706,912, filed Aug. 9, 2005, the contents of which is are hereby incorporated by reference.

FIELD OF THE INVENTION

The present invention relates to methods and compositions for the treatment of diseases and disorders, including hyperproliferative disorders, cancer, inflammatory diseases or disorders of the immune system, comprising administering a TACI-Ig fusion protein which blocks functions of growth factors of the TNF family.

BACKGROUND OF THE INVENTION

The BlyS Ligand/Receptor Family

Three receptors, TACI (transmembrane activator or Calcium-Modulating Cyclophylin Ligand-interactor), BCMA (B-cell maturation antigen) and BAFF-R (receptor for B-cell activating factor, belonging to the TNF family), have been identified that have unique binding affinities for the two growth factors (BlyS (B-lymphocyte stimulator) and APRIL (a proliferation-inducing ligand) (Marsters et al. Curr Biol 2000; 10(13): 785-788; Thompson et al. Science 2001; 293: 21 08-2111). TACI and BCMA bind both BLyS and APRIL, while BAFF-R appears capable of binding only BLyS with high affinity (Marsters et al. Curr Biol 2000; 10(13):785-788; Thompson et al. Science 2001; 293:21 08-2111). As a result, BLyS is able to signal through all three receptors, while APRIL only appears capable of signaling through TACI and BCMA. In addition, circulating heterotrimer complexes of BLyS and APRIL (groupings of three proteins, containing one or two copies each of BLyS and APRIL) have been identified in serum samples taken from patients with systemic immune-based rheumatic diseases, and have been shown to induce B-cell proliferation in vitro (Roschke et al. J Immunol 2002; 169: 4314-4321). Amongst the Ig-fusion proteins for all three receptors, only TACI-Fc5 was able to block the biological activity of the heterotrimeric complexes (Roschke et al. J Immunol 2002; 169: 4314-4321).

BLyS and APRIL are potent stimulators of B-cell maturation, proliferation and survival (Gross et al. Nature 2000; 404: 995-999. Gross et al. Immunity 2001; 15(2): 289-302. Groom et al. J Clin Invest 2002; 109(1): 59-68). BLyS and APRIL may be necessary for persistence of autoimmune diseases, especially those involving B-cells. Transgenic mice engineered to express high levels of BLyS exhibit immune cell disorders and display symptoms similar to those seen in patients with Systemic Lupus Erythematosus (Cheson et al. Revised guidelines for diagnosis and treatment. Blood 1996; 87:4990-4997. Cheema et al. Arthritis Rheum 2001; 44(6): 1313-1319). Similarly, increased levels of BLyS/APRIL have been measured in serum samples taken from SLE patients and other patients with various autoimmune diseases like Rheumatoid Arthritis (Roschke et al. J Immunol 2002; 169:4314-4321; Mariette X., Ann Rheum Dis 2003; 62(2):168-171; Hahne et al. J Exp Med 1998; 188(6):1185-1190), extending the association of BLyS and/or APRIL and B-cell mediated diseases from animal models to humans.

B-Cell Neoplasms

B-cell neoplasms constitute a heterogeneous group of lymphoproliferative cancers with varied patterns of clinical behavior and responses to therapy. Overall prognosis can be predicted with reasonable accuracy by histologic type of tumor, stage of disease, and treatment previously received. Clinical outcomes are generally associated with the overall grade of disease. B-cell neoplasms occupy a spectrum of diseases ranging from indolent chronic lymphocytic leukemias that often evolve over years to highly aggressive lymphomas with much shorter time courses. Although ultimately incurable, indolent B-cell neoplasms tend to be associated with a relatively good prognosis, with median survival in the range of ten years.

More aggressive types of B-cell neoplasms can be cured with intensive combination chemotherapy regimens and approximately half of patients survive for at least 5 years. Although addition of Rituximab™ to therapeutic regimens has generally improved clinical outcomes, B-cell neoplasms frequently recur in the first two years after initial treatment. Remission is often achieved with retreatment if the disease histology remains low grade. Unfortunately, patients who present with or convert to aggressive forms of B-cell neoplasms have a poorer prognosis and represent an unmet medical need. Thus, there is a long-felt need in the art for developing more effective methods of treating B-cell neoplasms, including Hodgkin's and non-Hodgkin's lymphomas.

SUMMARY OF THE INVENTION

The invention includes methods of treating B-cell neoplasms. The methods of the invention include administering to a patient a composition comprising a human immunoglobulin-constant domain and TACI extracellular domain or a fragment thereof which binds BlyS and/or APRIL.

In one embodiment, the invention comprises methods of treating B-cell neoplasms, including non-Hodgkin's lymphoma, using a TACI-Ig fusion molecule that comprises the TACI extracellular domain or any fragment thereof that retains the ability to bind BlyS and/or APRIL.

In another embodiment, the invention comprises methods of treating non-Hodgkin's lymphoma comprising administering to a patient a fusion molecule comprising a human immunoglobulin-constant chain and TACI extracellular domain or a fragment of TACI extracellular domain that binds BlyS and/or APRIL. One preferred fragment of the extracellular domain of TACI comprises one or two cysteine repeat motifs. Another preferred fragment is a fragment comprising amino acids 30-110 of the extracellular domain of TACI. Yet another preferred fragment is a fragment comprising amino acids 1-154 of the extracellular domain of TACI (SEQ ID NO: 1).

In another embodiment, the invention comprises methods of treating non-Hodgkin's lymphoma by administering to a patient a composition comprising a fusion polypeptide, TACI-Fc5, comprising a human immunoglobulin-constant domain, Fc5, having the sequence set out as SEQ ID NO: 2 and a TACI extracellular domain having the sequence set out as SEQ ID NO: 1.

In still another embodiment, the invention comprises methods of treating non-Hodgkin's lymphoma by administering to a patient a composition comprising a fusion polypeptide comprising a human immunoglobulin-constant domain with the sequence set out as SEQ ID NO: 2 and a polypeptide which binds BlyS and/or APRIL and which is at least 50% identical, preferably 60%, 65%, 70%, 75%, 80%, 85%, 90%, 95% or 99% identical to SEQ ID NO: 1.

Other B-cell malignancies that can be treated by the methods of invention by administering to a patient a fusion polypeptide comprising a human immunoglobulin-constant chain and TACI extracellular domain or a fragment of TACI extracellular domain that binds BlyS and/or APRIL. Such B-cell malignancies include, but are not limited to, acute leukemia, acute lymphocytic leukemia, acute myelocytic leukemia, myeloblastic leukemia, promyelocytic leukemia, myelomonocytic leukemia, monocytic erythroleukemia, chronic leukemia, chronic myelocytic (granulocytic) leukemia, chronic lymphocytic leukemia, polycythemia vera, Hodgkin's disease, multiple myeloma, and Waldenstrom's macroglobulinemia.

In one preferred embodiment, the methods of the instant invention comprise administering to a non-Hodgkin's lymphoma patient a TACI-Ig fusion molecule in amounts from 0.01 mg per 1 kg of patient's body weight to 10 mg per 1 kg of patient's body weight. The TACI-Ig fusion molecule can be administered repeatedly at predetermined intervals. Preferably, the molecule is administered at least 5 times during a four-week interval. This initial treatment with a TACI-Ig fusion polypeptide can be followed by administering the polypeptide on weekly basis at least during 2 more additional weeks, and more preferably the polypeptide is administered on weekly basis for additional 2 to 30 weeks.

According to the methods of the instant invention, a TACI-Ig fusion polypeptide can be administered to a non-Hodgkin's lymphoma patient subcutaneously, orally or intravenously and optionally in combination with other medicaments. Such medicaments include, but are not limited to, bisphosphonate, erythropoietin, granulocyte growth factors, granulocyte colony stimulating factor, drugs for the management of pain, melphalan, vincristine, doxorubicin, thalidomide and nucleoside analogs.

In one embodiment of the invention, TACI-Ig is administered in combination with bortezomib. TACI-Ig can be dosed as described above and bortezomib is given at a dose of about 1.3 mg/m$^2$ twice weekly for two weeks, followed by a rest period of ten days. This represents one cycle of treatment. Optionally, bortezomib can be administered intravenously. The response to treatment is monitored as described above for TACI-Ig alone, and additional treatment cycles of TACI-Ig and/or bortezomib may be administered. TACI-Ig may be administered at a dose as described above or at a lower dose in combination with bortezomib at a dose described herein or at a lower dose of bortezomib. Doses of TACI-Ig and bortezomib may be given concurrently or in alternating doses of TACI-Ig followed by a cycle of bortezomib or a cycle of bortezomib followed by a cycle of TACI-Ig. This dosing may be repeated.

TACI-Ig may be administered to those patients who have become resistant to or who do not respond to other methods of treatment, including but not limited to treatment with bortezomib.

These and other embodiments of the present invention are described in further detail herein below.

BRIEF DESCRIPTION OF THE DRAWINGS

FIG. 1. Dose-escalation decision tree for TACI-Fc5 treatment.

FIG. 2. Diagram of patient's body areas that can be used for subcutaneous injections of TACI-Ig molecule.

FIG. 3. SEQ ID NO: 1
FIG. 4. SEQ ID NO: 2

DETAILED DESCRIPTION OF THE INVENTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the art of pharmaceutical sciences or the art relevant to the range or element at issue. Also, the disclosure of ranges is intended as a continuous range including every value between the minimum and maximum values recited as well as any ranges that can be formable thereby.

The instant invention pertains to methods of ameliorating abnormal proliferation of hematopoetic cells in a patient by inhibiting interaction of BlyS and/or APRIL with their receptors. Specifically, the methods utilize an inhibitor that comprises 1) a polypeptide that comprises a domain which is at least partially identical to TACI extracellular domain or a fragment thereof and binds BlyS and/or APRIL and 2) a human immunoglobulin constant chain. The methods of the invention utilize a fusion molecule comprising a human immunoglobulin constant chain and any polypeptide with at least 50% sequence identity to TACI extracellular domain that can bind BlyS and/or APRIL ligands, and preferably 60%, 65%, 70%, 75%, 80%, 85%, 90%, 95% or 99% identity to TACI extracellular domain. U.S. Pat. Nos. 5,969,102, 6,316,222 and 6,500,428 and U.S. patent application Ser. Nos. 09/569,245 and 09/627,206 (teachings of which are incorporated herein in their entirety by reference) disclose sequences for the extracellular domain of TACI as well as specific fragments of the TACI extracellular domain that interact with TACI ligands, including BlyS and APRIL. One preferred fragment of the extracellular domain of TACI comprises one or two cysteine repeat motifs. Another preferred fragment is a fragment comprising amino acids 30-110 of the extracellular domain of TACI. Yet another preferred fragment is a fragment comprising amino acids 1-154 of the extracellular domain of TACI (SEQ ID NO: 1).

Other fusion molecules useful for the methods of the invention include: a fusion polypeptide between a human immunoglobulin constant chain and the complete TACI extracellular domain or its ortholog or a fusion polypeptide between a human immunoglobulin constant chain and any fragment of the extracellular TACI domain that can bind BlyS and APRIL ligands. Any of the fusion molecules used in the methods of the invention can be referred to as a TACI-Ig fusion molecule.

TACI-Fc5 is one of the TACI-Ig fusion molecules useful for the methods of the invention. TACI-Fc5 is a recombinant fusion polypeptide comprising the extracellular, ligand-binding portion of receptor TACI from about amino acid 1 to about amino acid 154 (SEQ ID NO: 1) and the modified Fc portion of human IgG, Fc5 (SEQ ID NO: 2). Other TACI-Ig molecules useful for the methods of the instant invention include a fusion molecule comprising polypeptide with SEQ ID NO: 2 and a polypeptide which can bind BlyS and which is at least 50% identical, preferably 60%, 65%, 70%, 75%, 80%, 85%, 90%, 95% or 99% identical to SEQ ID NO: 1.

Embodiments of the instant invention comprise methods of using a TACI-Ig fusion molecule for treating non-Hodgkin's lymphoma. Other hematological malignancies that can be treated with the methods of the invention include leukemias (acute leukemia, acute lymphocytic leukemia, acute myelocytic leukemia, myeloblastic leukemia, promyelocytic leukemia, myelomonocytic leukemia, monocytic erythroleukemia, chronic leukemia, chronic myelocytic (granulocytic) leukemia, chronic lymphocytic leukemia, polycythemia vera), lymphomas (Hodgkin's disease, multiple myeloma, Waldenstrom's macroglobulinemia and heavy chain disease), autoimmune diseases such as rheumatoid arthritis and systemic lupus erythematosus or to decrease the number of circulating mature B-cells and immunoglobulin-secreting cells and soluble immunoglobulins associated with such diseases.

Embodiments also comprise methods of treatment by administering to a patient a fusion molecule comprising a human immunoglobulin-constant domain and a polypeptide comprising any fragment of TACI extracellular domain that can bind BlyS and/or APRIL.

A TACI-Ig fusion molecule can be administered to a patient orally, intravenously or subcutaneously.

TACI-Ig formulations useful for the methods of the invention can be prepared and stored as a frozen, sterile, isotonic solution. Such formulations can include other active ingredients and excipients such as, for example, sodium chloride, phosphate buffer and sodium hydroxide or O-phosphoric acid (pH 6.0). TACI-Ig formulations can be administered to a patient in combination with other medicaments. Such medicaments include, but are not limited to, bisphosphonate, erythropoietin, granulocyte growth factors, granulocyte colony stimulating factor and drugs for the management of pain. Methods of the invention can be used in combination with other methods of treating B-cell neoplasms. Such other methods of treatment include, but are not limited to, chemotherapy, radiotherapy and gene therapy. TACI-Ig formulations can be administered prior, simultaneously or more preferably, subsequently to other methods of treatment.

TACI-Fc5 has been shown to inhibit BLyS activation of B cell proliferation in vitro. Treatment of mice with TACI-Fc5 results in a partial block in B cell development that has a minimal effect on B cell precursors in the bone marrow and other cell lineages including peripheral blood T cells, monocytes and neutrophils. Transgenic mice engineered to over-express a soluble form of the TACI receptor in the blood produce fewer mature B cells and show reduced levels of circulating antibody. The TACI-Fc5 transgenic mice had normal numbers of cells in the thymus, bone marrow and mesenteric lymph node. There were no significant differences in T cell populations in the thymus, lymph node and spleen. (Gross et al. Immunity 2001; 15(2): 289-302.)

Further, TACI-Ig can inhibit antigen-specific antibody production in an immune response in mice whether administered during the primary response or the secondary response to an antigen. In these studies, no effect on T cell response to ex vivo antigenic challenge was observed. In an animal model of systemic lupus erythematosus, treatment with TACI-Ig fusion proteins was effective in limiting the onset and progression of the disease. (Gross et al. Nature 2000; 404: 995-999). Similarly, in a mouse model of collagen-induced arthritis, TACI-Ig was able to inhibit the development of collagen-specific antibodies and reduce both the incidence of inflammation and the rate of occurrence of disease. (Gross et al. Immunity 2001; 15(2): 289-302.)

A composition comprising a TACI-Ig fusion molecule can be administered to a patient repeatedly during a four-week period of time. For example, a patient may receive five subcutaneous injections of TACI-Ig molecule during this period on a schedule disclosed in Table 5. The four-week period of treatment is then followed by a four-week follow-up period (Table 5). Example 3 provides further details of this protocol.

TABLE 5

Schedule of treatment with a TACI-Ig fusion molecule

| | | Dosing Days (+/−1 day) | | | | | Follow-up Days (+/−1 day) | | | |
|---|---|---|---|---|---|---|---|---|---|---|
| Event | Screen | Day 1 | Day 7 | Day 14 | Day 21 | Day 28 | Day 35 | Day 42 | Day 49 | Day 56 |
| ICF/Dem/Med Hist/Preg | X | | | | | | | | | |
| Weight/Height | | X | | | | | | | | X |
| Interval History/PE | X | X | X | X | X | X | X | X | X | X |
| VS[1] | X | X | X | X | X | X | X | X | X | X |
| Hematology | X | X | X | X | X | X | X | X | X | X |
| Serum Chemistry | X | X | X | X | X | X | X | X | X | X |
| Coagulation Panel | | X | | X | | | X | | | X |
| Flow cytometry | X | X | X | X | X | X | X | X | X | X |
| Immunoglobulins | X | X | | X | | X | | X | | X |
| Urinalysis | X | | | | | | | | | X |
| ECOG | X | | | | | | | | | X |
| Tumor restaging[2] | X | | | | | | | | | X |
| PK[3] | | X | X | X | | X | | X | | |
| Tumor Biopsy[4] | X | | | | | | | | | X |
| Anti-TACI antibody[7] | | X | | | | | | | | X |
| PD[5] | X | X | | X | | X | | X | | X |

TABLE 5-continued

Schedule of treatment with a TACI-Ig fusion molecule

| | | Dosing Days (+/−1 day) | | | | Follow-up Days (+/−1 day) | | | |
|---|---|---|---|---|---|---|---|---|---|
| Event | Screen | Day 1 | Day 7 | Day 14 | Day 21 | Day 28 | Day 35 | Day 42 | Day 49 | Day 56 |
| Adverse Events and Con Meds and Procs[6] | X | X | X | X | X | X | X | X | X | X |

[1]Vital Signs will be taken prior to each dose of TACI-FC5. Post-administration VS for the first dose of TACI-Fc5 will be taken at 1 hour, 2 hours, 4 hours and 8 hours. All other subsequent doses will be taken at 1 hour and 2 hours.
[2]Screening CT and PET Scans performed no more than 21 days prior to treatment; restaging studies within 5 days of Day 56. See Study Operations Manual for measurement of tumor specific indicators of disease burden and evaluation of marrow (if indicated).
[3]Day 1 at pre-dose, 2 h., 4 h and 8 h, then at 24 (day 2), 48 (day 3), 72 (day 4), 168 (day 7), 336 (day 14), 672 (day 28), and 1008 (day 42) hrs. The values before the second dose (168 h, day 7), the third dose (336 h, day 14), and the fifth dose (672 h, day 28) are trough concentrations by design.
[4]If consent obtained and deemed appropriate by investigator. Study Operations Manual outlines tissue collection and study procedures.
[5]Study Operations Manual outlines collection of additional research pharmacodynamic markers: serum levels of free APRIL and BlyS and BLyS/TACI FcS complex.
[6]Subjects will be followed for recovery of both lymphocyte and immunoglobulin classes to either pretreatment baseline levels or absolute lymphocyte count > 800/mm$^3$, IgG > 400 mg/dL, IgA > 65 mg/dL and IgM > 40 mg/dL. During periods of extended follow-up of immunologic recovery, the incidence, type and severity of infections will be documented
[7]Anti-TACI antibodies will also be collected at Day 85 on patients not entering the extension study.

Patients who demonstrate improvement or at least stabilization of their condition, may be treated with a TACI-Ig fusion molecule for additional period of time. For example, these patients may be administered a weekly dose of a TACI-Ig fusion molecule for additional 2 to 30 weeks. Table 6 provides an exemplary extended schedule for administering TACI-Ig molecule to patients.

TABLE 6

Schedule for extended treatment with a TACI-Ig molecule (Part 1).

| Event | Pre | Week 1 | Week 2 | Week 3 | Week 4 | Week 5 | Week 6 | Week 7 | Week 8 | Week 9 | Week 10 | Week 11 | Week 12 |
|---|---|---|---|---|---|---|---|---|---|---|---|---|---|
| Informed Consent/Pregnancy test | X | | | | | | | | | | | | |
| TACI Administration | | X | X | X | X | X | X | X | X | X | X | X | X |
| Height & Weight | X | | | | | | | | | | | | |
| Interval History[1] | X | | X | | X | | X | | X | | X | | X |
| PE w/VS | X | | X | | X | | X | | X | | X | | X |
| Hematology | X | | X | | X | | X | | X | | X | | X |
| Serum Chemistry | X | | | | X | | | | X | | | | X |
| Coagulation Panel | X | | | | X | | | | X | | | | X |
| Flow cytometry | X | | | | X | | | | X | | | | X |
| Immunoglobulins | X | | | | X | | | | X | | | | X |
| Urinalysis | X | | | | | | | | | | | | |
| ECOG | X | | | | | | | | | | | | |
| Tumor restaging[2] | X | | | | | | | | | | | | X |
| PK | X | | | | X | | | | X | | | | X |
| Anti-TACI antibody | X | | | | | | | | | | | | X |
| PD[3] | X | | | | X | | | | X | | | | X |
| Adverse Events and Concomitant Medications | X | | | | | | ONGOING | | | | | | |
| Blood Volume per visit | X | | | | X | | | | X | | | | X |

Part 2

| Event | Week 13 | Week 14 | Week 15 | Week 16 | Week 17 | Week 18 | Week 19 | Week 20 | Week 21 | Week 22 | Week 23 | Week 24 | Final Visit Week 28 |
|---|---|---|---|---|---|---|---|---|---|---|---|---|---|
| TACI Administration | X | X | X | X | X | X | X | X | X | X | X | X | |
| Weight | | | | | | | | | | | | X | |
| Interval History[1] | | X | | X | | X | | X | | X | | X | |
| PE w/VS | | X | | X | | X | | X | | X | | X | |
| Hematology | | X | | X | | X | | X | | X | | X | |
| Serum Chemistry | | | | X | | | | X | | | | X | |
| Coagulation Panel | | | | X | | | | X | | | | X | |
| Flow cytometry | | | | X | | | | X | | | | X | X[4] |
| Immunoglobulins | | | | X | | | | X | | | | X | X[4] |
| ECOG | | | | | | | | | | | | X | |
| Urinalysis | | | | | | | | | | | | X | |
| Tumor restaging[2] | | | | | | | | | | | | X | |
| PK | | | | X | | | | X | | | | X | |

TABLE 6-continued

Schedule for extended treatment with a TACI-Ig molecule (Part 1).

| | | | |
|---|---|---|---|
| Anti-TACI antibody | | | X |
| PD[3] | X | X | X |
| Adverse Events and Concomitant Medications | | ONGOING | |
| Blood Volume per visit | X | X | X |

[1]All clinic visits may be +/−3 days.
[2]Restaging scans to be performed at week 12 and then at approximately week 24 or at time of discontinuation, whichever is first. See Study Operation Manual for measurement of tumor specific indicators of disease burden and evaluation of marrow (if indicated).
[3]Study Operation Manual outlines collection of additional research pharmacodynamic markers: Serum levels of free APRIL and BLyS and BLyS/TACI Fc5 complex.
[4]Subjects who demonstrate recovery of both lymphocyte and immunoglobulin classes to either pretreatment baseline levels or absolute lymphocyte count > 800/mm³, IgG > 400 mg/dL, IgA > 65 mg/dL and IgM > 40 mg/dL are formally off study once they complete the 28 day safety follow-up after the final dose of TACI-Fc5. Subjects who fail to meet these levels will have complete blood counts and IgG, IgA and IgM levels assessed monthly until recovery is documented as defined above. During this extended follow-up, the incidence, type and severity of infections will also be documented A TACI-Ig fusion molecule is administered to a patient in amount that is efficient for treating patient's condition. The amount may range from 0.01 mg per 1 kg of patient's body weight to 10 mg per 1 kg of patient's body weight. An optimal dose for treating with a TACI-Ig fusion molecule can be developed by using a diagram of FIG. 1, described in further detail in Example 5.

A fusion TACI-Ig molecule may be delivered via subcutaneous injections into the anterior abdominal wall. When more than one injection is required to administer a dose, the injections must be administered a few centimeters apart and as close as possible in time. For the repeated drug administration it is advised to rotate the site of administration on the anterior abdominal wall. The possible zones for subcutaneous injection into the anterior abdominal wall are depicted in FIG. 2 and include right upper external area, left lower external area, right lower external area, left upper external area, median lower area as well as right and left thighs and upper arms (FIG. 2). Alternatively, a TACI-Ig fusion molecule of the instant invention may delivered via intravenous injections or orally in a form of tablets, caplets, liquid compositions or gels.

Methods of the invention can be combined with other methods of cancer treatment such as chemotherapy, radiation or surgery. A TACI-Ig fusion molecule of the invention can be administered after a cancer patient completes chemotherapy, radiation and/or surgery. A TACI-Ig fusion molecule of the invention can be administered concomitantly with other medications beneficial for a patient. Such medications may include, but are not limited, to bisphosphonates, erythropoietin, granulocyte growth factors or granulocyte colony stimulating factor or drugs for the management of pain, melphalan, vincristine, doxorubicin, thalidomide and nucleoside analogs.

In one embodiment of the invention, TACI-Ig is administered in combination with bortezomib. TACI-Ig can be dosed as described above and bortezomib is given at a dose of about 1.3 mg/m² twice weekly for two weeks, followed by a rest period of ten days. This represents one cycle of treatment. Optionally, bortezomib can be administered intravenously. The response to treatment is monitored as described above for TACI-Ig alone, and additional treatment cycles of TACI-Ig and/or bortezomib may be administered. TACI-Ig may be administered at a dose as described above or at a lower dose in combination with bortezomib at a dose described herein or at a lower dose of bortezomib. Doses of TACI-Ig and bortezomib may be given concurrently or in alternating doses of TACI-Ig followed by a cycle of bortezomib or a cycle of bortezomib followed by a cycle of TACI-Ig. This dosing may be repeated.

TACI-Ig may be administered to those patients who have become resistant to or who do not respond to other methods of treatment, including but not limited to treatment with bortezomib.

All U.S. patents and published patent applications listed herein are hereby incorporated by reference in their entirety.

EXAMPLES

The following examples illustrate various embodiments of the present invention are not to be construed as limiting the invention in any way.

Example 1

Testing TACI-Fc5 Pharmacology, Toxicology and Pharmacokinetics in Experimental an Animal Model TACI-Fc5 was evaluated in a host resistance model that provided the opportunity to directly assess the functional reserve of the immune system. Mice were challenged with influenza virus during TACI-Fc5 treatment. Dexamethasone, used as a positive control, resulted in an enhanced and prolonged viral infection. TACI-Fc5 reduced circulating B cells, total IgG and IgM, and influenza-specific IgG and IgM, but did not decrease the animals' ability to clear the viral infection.

Pivotal Safety Pharmacology studies showed that TACI-Fc5 induced no major changes of the nervous, respiratory and cardiovascular systems in mice or monkeys up to the SC dose of 80 mg/kg. Only in mice, a slightly increased hyperalertness and locomotor activity, that may suggest minor and transient stimulant effect, was seen at 80 mg/kg, with a No-observed effect level (NOEL) equal to 20 mg/kg.

When administered to mice as a single dose by the intravenous (IV) or subcutaneous (SC) route, TACI-Fc5 did not induce mortality or appreciable general or local abnormal effects in the animals up to the highest technically feasible dose: 1200 mg/kg.

The administration to monkeys of TACI-Fc5 as a single dose by the SC route at the dose level of 240 mg/kg did not result in mortality or in any major toxic effects.

On the basis of the results obtained after 2 or 4 weeks of administration of TACI-Fc5 by subcutaneous route to mice at the doses of 5, 20 and 80 mg/kg/every second day, it may be concluded that the compound is well tolerated in this species at doses up to 80 mg/kg. Treatment-related modifications confined to the immune system were revealed at all doses. These changes involved decreases in total and mature B cell numbers and IgG and IgM serum levels. Immunohistochemistry tests done in the spleen and lymph nodes confirmed depletion confined to B cells, with T cell number being unchanged. All these alterations, time- and dose-related in some cases, were considered as exaggerated pharmacological effects as expected in a responsive species after administration of very high doses of TACI-Fc5. Overall, these effects were seen after 2 and 4 weeks of treatment, without major indications of progression with time. They appeared to be almost completely reversible after 4 weeks of withdrawal of treatment, except for decreased B cell counts.

In order to ascertain B-cell modulation reversibility, a further study in mice was conducted at the doses of 5 and 20 mg/kg given for 4 weeks every 2nd day, with longer recovery periods. Recovery of total and mature circulating B cells was reached after two months of withdrawal at 5 mg/kg, and after 4 months at 20 mg/kg. Moreover, the injection induced a slight increase, compared to vehicle controls, of inflammatory changes at the injection sites at all doses.

Subcutaneous administration of TACI-Fc5 in monkeys did not induce major signs of toxicity at any of the doses tested: 5, 20 or 80 mg/kg/every 3rd day, when given for four consecutive weeks.

Local tolerability was considered satisfactory up to and including the highest dose tested. Dose-related and reversible slight or moderate changes of inflammatory origin (mainly perivascular mononuclear and eosinophilic cell infiltrates) were induced, but were considered mainly related to the local presence of exogenous proteins. Only at the high dose, a few animals showed slight or moderate subacute inflammation associated with a cyst formation in one of them.

Circulating B-cell number decreases at the lymphocyte subset determinations, as well as histological depletion of the spleen follicular marginal zone (known to be a B-cell dependent area) and decreases in total IgG and IgM serum levels were seen. They were considered a result of the pharmacodynamic properties of TACI-FcS, as shown by in vitro and in vivo pharmacology experiments. Their degree was exaggerated, as expected in toxicology studies in which animals are purposely administered high doses of the test compound. While low serum IgG and IgM levels and spleen lymphocytic depletion showed a clear tendency towards recovery within the one month withdrawal period allowed, total and mature circulating B cells did not show a similar behavior, indicating a longer time needed to recover.

At the end of the treatment period (week four), males and females of the high dose group (80 mg/kg) showed a slight but statistically significant decrease in mean total protein values compared to controls. A slight trend towards decrease was also seen at the same dose in week two, and at the end of the recovery period.

Serum protein modifications in the high dose females at the end of the dosing period included a decrease in globulin and increases in albumin percentage and alpha-1-globulin fraction. Alpha-1-globulin fraction also appeared higher than controls in group 3 females (20 mg/kg).

Immunogenicity of TACI-FcS was low in both mice (only a few females showed low levels of circulating binding antibodies during and after the treatment period) and monkeys (low levels were found after the recovery period in a few animals); there was no evidence of neutralizing antibodies in either species.

TACI-Fc5 was tested with the standard battery of in vivo tests to detect toxicology of reproduction and fertility (fertility test in male and female mice, treated by sc route at the doses of 5, 20 and 80 mg/kg/every 2nd day before and during the mating and up to the implantation period) and embryo-fetal development (embryo-fetal development study in female mice and rabbits, treated by sc route at the doses of 5, 20 and 80 mg/kg/every 2nd day during the organogenesis period).

The fertility test in mice showed a dose-related increase in pre- and post-implantation losses following exposure to 20 and 80 mg/kg/every 2nd day of TACI-Fc5 compared to the control group.

Evaluation of the data obtained in mice of the embryo-fetal development study showed that no embryo-toxic effects were seen at any dose, and no compound-related fetal malformations were induced.

In rabbits, the embryo-fetal development study showed that treatment caused a dose-related lower body weight gain and lower food consumption in the pregnant animals treated with 20 or 80 mg/kg/every 2nd day. The above maternal changes were associated with an increased rate of resorptions and lower fetal body weight at the two higher doses.

These results suggest a possible effect of TACI-Fc5 on implantation of the mouse blastocyst in the uterus. The observed effects of TACI-Fc5 on maternal weight gain and food consumption were likely responsible for the observed effects on litter viability in rabbits exposed to 20 or 80 mg/kg/every 2nd day during organogenesis and that there is no direct toxicity of TACI-Fc5 on the fetus. No malformations were attributed to TACI-Fc5 treatment in these two animal species.

In addition, histological examination of male and female gonads and accessory sex organs was conducted in the 2-week and 1-month toxicity studies done by sc route in mice and monkeys in which TACI-Fc5 was administered every 2nd or every 3rd day, respectively, without evidence of treatment-related effects.

The local tolerance study in rabbits showed that TACI-Fc5 formulation was well tolerated locally when injected by the subcutaneous route to rabbits, at the dose of 70 mg/mL.

A single dose pharmacokinetic study in male mice by IV and SC routes was conducted in mice by either the intravenous route, at the dose of 1 mg/kg, or the subcutaneous route, at the doses of 1, 5 and 15 mg/kg.

Time to maximal absorption ($t_{max}$) was estimated between 4 hours to 16 hours, with a $t_{1/2}$ calculated to be around 40-50 hours.

An infusion-like profile was observed during the first 30 minutes after IV bolus administration, after which TACI-Fc5 was eliminated from the body with an elimination half-life of 44 hours. After subcutaneous administration, the ratio between the AUCs (Area Under the Curve) obtained at the 3 doses of 1, 5 and 15 mg/kg was 1:5:8 vs. the dose ratio of 1:5:15, suggesting a loss of dose-proportionality at the high dose.

TACI-Fc5's bioavailability by the subcutaneous route was of 76 and 89% at the doses of 1 and 5 mg/kg, but was lower than expected at 15 mg/kg (0.42; calculated vs. the intravenous 1 mg/kg dose) in mice. Since the apparent elimination half-life was not altered, the lower bioavailability observed at the high dose could be explained by an increase of both clearance and volume of distribution or more probably by a decreased absorption due to the formation of a deposit at the site of injection.

A single dose pharmacokinetic study in male monkeys by IV and SC routes was conducted in male cynomolgus monkeys injected by either the intravenous route, at the dose of 1 mg/kg, or the subcutaneous route, at the doses of 1, 5 and 15 mg/kg.

Six male monkeys were divided into 2 groups of 3 animals each and received 2 administrations separated by a wash-out period of two weeks. Treatments of period 1 were 1 mg/kg IV (group 1) and 1 mg/kg SC (group 2) and treatments of period 2 were 5 mg/kg SC (group 1) and 15 mg/kg SC (group 2).

Time to maximal absorption ($t_{max}$) was estimated between 6 hours to 8 hours, with a $t_{1/2}$ calculated to be around 120-190 hours.

An infusion-like profile was observed in 2 out of 3 monkeys during the first 15 min after IV bolus administration, after which TACI-Fc5 was eliminated from the body with an elimination half-life of 179±29 hours. The volume of distribution at the steady state, Vss, was 382±82 mL/kg, a volume near the intracellular fluid volume.

After subcutaneous administration, the AUC vs. dose proportionality was good, i.e. 216, 1182 and 2732 h µg/mL for SC doses of 1, 5 and 15 mg/kg. The TACI-Fc5 bioavailability by the subcutaneous route (calculated vs. the 1 mg/kg IV dose) was 0.92, 1.02 and 0.77 at the low, intermediate and high doses. Therefore, TACI-Fc5 was almost completely absorbed by the subcutaneous route.

Low levels of TACI-Fc5 were found in the pre-dose samples for period 2 (between doses of 1 mg/kg by IV or SC routes, period 1, and doses of 5 or 15 mg/kg, respectively, in period 2) for all six monkeys, since during the 2-week washout period only 2 half-lives had elapsed, which was insufficient for a complete elimination of the administered compound (5 half-lives required). However, the AUC contribution of the previous dose could be estimated to represent only about 2% of the total AUC in period 2.

IgG serum levels showed a 10.2% decrease after IV dosing. The 15 mg/kg SC dose showed a slightly higher effect, while no differences were observed between the 1 and the 5 mg/kg SC doses (decreases of 8.6%, 8.4% and 12.3% after 1, 5 and 15 mg/kg doses respectively). IgM serum levels showed an 18.0% decrease after IV dosing. No differences were observed between the 3 SC doses (decreases of 23.5%, 23.0% and 24.2% after 1, 5 and 15 mg/kg doses respectively).

Example 2

Determining TACI-Fc5 Tolerable Dose in Healthy Volunteers

The first phase I study of TACI-Fc5 is currently being completed. This is a double-blind, placebo controlled, dose escalating, sequential dose study investigating the safety, pharmacokinetics and pharmacodynamics of single doses of TACI-Fc5 administered subcutaneously to healthy male volunteers. An outline of the study design is presented below, along with summaries of the available data.

TACI-Fc5 was administered to humans for the first time; this was a double-blind, placebo controlled, dose escalating, sequential dose study investigating the safety, pharmacokinetics and pharmacodynamics of single doses of TACI-Fc5 administered subcutaneously to healthy male volunteers.

Four groups of subjects were recruited. In each dosing group one subject was randomized to receive a placebo injection, with all others receiving TACI-Fc5. Following discharge from the investigational site at 24 hours post dose, subjects attended on an outpatient basis for seven weeks of scheduled assessments. Systemic and local tolerability of TACI-Fc5 were monitored by physical examination findings, injection site pain, local tolerability reactions at the site of injection(s) (redness, swelling, bruising and itching), vital signs, 12-lead ECGs (electrocardiograms), safety laboratory assessments and recording of adverse events.

Pharmacokinetic and pharmacodynamic markers were monitored throughout the seven-week period following dosing. The pharmacodynamic effect of TACI-Fc5 was monitored using a number of markers including: lymphocyte subsets by FACS analysis (plasma cells (CD138+), immature B cells (CD19+, IgD−), mature B cells (CD19+, IgD+), T-helper cells (CD5+, CD4+), cytotoxic T-cells (CD5+, CD8+), total T-cells (CD5+)), free BlyS, BlyS/TACI-Fc5 complex, IgG, IgM, anti-TACI-Fc5 antibodies.

Dose escalation was guided by an algorithm within the study protocol, base upon a review of data three weeks after dosing. Four groups were dosed: group 1 received 2.1 mg; group 2 received 70 mg; group 3 received 210 mg and group 4 received 630 mg.

Results: healthy male volunteers were administered single subcutaneous doses of TACI-Fc5 at doses ranging from 0.03 mg/kg to 9 mg/kg. Safety and tolerability data have been used, together with FACS analysis of lymphocyte subsets at week 3, to guide the dose escalation between cohorts. Four cohorts have been studied, as shown in Table 1.

TABLE 1

Repartition of volunteers

| Cohort Number | Number of Subjects[C] | Dose Level | Administered Dose[a] |
|---|---|---|---|
| 1 | 6 | 0.03 mg/kg[b] | 2.1 mg |
| 2 | 6 | 1 mg/kg | 70 mg |
| 3 | 6 | 3 mg/kg | 210 mg |
| 4 | 5[d] | 9 mg/kg | 630 mg |

[a]At each dose level a nominal weight of 70 kg was assumed, with subjects receiving a standardized dose.
[b]Due to a dilution error the dose administered to cohort 1 was 10 fold lower than had been planned (0.3 mg/kg). This error was identified upon review of pharmacokinetic data from cohort 1, but following dosing of cohort 2.
[c]including 1 subject on placebo.
[d]One volunteer withdrew before the injection took place Demographic baseline characteristics were summarized for the population by cohort and overall and are shown in Table 2.

TABLE 2

Demographic Characteristics

| Characteristic | Statistics | | Cohort 1 | Cohort 2 | Cohort 3 | Cohort 4 | Total |
|---|---|---|---|---|---|---|---|
| Age (years) | n | (SD) | 6 | 6 | 6 | 5 | 23 |
| | Mean | | 30.2 (7.0) | 33.0 (7.7) | 25.3 (6.8) | 35.0 (5.4) | 30.7 (7.4) |
| | Range | | 23-43 | 23-43 | 19-34 | 30-44 | 19-44 |
| Body Mass | n | | 6 | 6 | 6 | 5 | 23 |
| Index | Mean | (SD) | 24.7 (1.7) | 26.0 (2.0) | 24.0 (3.5) | 25.3 (2.8) | 24.8 (2.4) |
| (kg/m2) | Range | | 22.2-26.6 | 23.1-28.9 | 18.7-28 | 22.3-27.5 | 18.7-28.9 |
| Height (m) | n | | 6 | 6 | 6 | 5 | 23 |
| | Mean | (SD) | 1.82 (0.04) | 1.80 (0.08) | 1.77 (0.07) | 1.73 (0.06) | 1.78 (0.07) |
| | Range | | 1.77-1.88 | 1.71-1.91 | 1.67-1.85 | 1.68-1.78 | 1.67-1.91 |

TABLE 2-continued

Demographic Characteristics

| Characteristic | Statistics | | Cohort 1 | Cohort 2 | Cohort 3 | Cohort 4 | Total |
|---|---|---|---|---|---|---|---|
| Weight (kg) | n | | 6 | 6 | 6 | 5 | 23 |
| | Mean | (SD) | 81.7 (7.3) | 84.2 (12.1) | 74.7 (7.6) | 76.2 (9.2) | 79.0 (9.4) |
| | Range | | 71-91 | 69-101 | 67-84 | 63-89 | 63-101 |
| Sex n (%) | n | | 6 | 6 | 6 | 5 | 23 |
| | Male | | 6 (100%) | 6 (100%) | 6 (100%) | 5 (100%) | 23 (100%) |
| | Range | | 0 (0%) | 0 (0%) | 0 (0%) | 0 (0%) | 0 (0%) |
| Race n (%) | n | | 6 | 6 | 6 | 5 | 23 |
| | White | | 6 (100%) | 6 (100%) | 6 (100%) | 5 (100%) | 23 (100%) |
| | Other | | 0 (0%) | 0 (0%) | 0 (0%) | 0 (0%) | 0 (0%) |

Overall, mean+:SD age was 30.7+7.4 years and the mean body mass index was 24.8 kg/m2. All volunteers were white males. TACI-Fc5 was well tolerated in all groups. There were no apparent effects upon physical examination findings, vital signs or 12-lead ECGs.

TACI-Fc5 is believed to have shown good tolerability at doses up to 630 mg with no significant safety concerns being raised. These data support the intended doses of the proposed subject studies.

TABLE 3

List of Treatment-Emergent Adverse Events Reported tn Date

| | | Treatment | | | | | | |
|---|---|---|---|---|---|---|---|---|
| Body System | Preferred Term | TACI-Fc5 2.1 mg N | TACI-Fc5 70 mg N | TACI-Fc5 210 mg N | TACI-Fc5 630 mg N | Placebo N | Total N | % |
| Eye Disorders | Eyelid Oedema | 1 | | | | | 1 | 2.1 |
| Gastrointestinal disorders | Abdominal pain upper | | | | | | 1 | 2.1 |
| | Diarrhoea | | 1 | 1 | 1 | 1 | 4 | 8.5 |
| | Mouth ulceration | | | | 1 | 1 | 2 | 4.3 |
| | Nausea | | 1 | | 1 | 1 | 3 | 6.4 |
| | Vomiting | | | 1 | 1 | | 2 | 4.3 |
| General disorders and administration site conditions | Influenza-like illness | | | | 1 | 2 | 3 | 6.4 |
| Infections and infestations | Nasopharyngitis | | 4 | 1 | 1 | | 6 | 10.6 |
| | Perianal abscess | 1 | | | | | 1 | 2.1 |
| Injury, poisoning and procedural complications | Contusion | | | | | 1 | 1 | 2.1 |
| | Joint Injury | | | 1 | | | 1 | 2.1 |
| Musculoskeletal and connective tissue disorders | Arthralgia | | 1 | | | | 1 | 2.1 |
| | Back Pain | | | | | 1 | 1 | 2.1 |
| Nervous system disorders | Headache | 1 | 2 | 2 | 2 | 1 | 8 | 17.0 |
| Respiratory, thoracic and mediastinal disorders | Cough | | 1 | | 1 | 1 | 3 | 6.4 |
| | Nasal congestion | | | 1 | | 1 | 2 | 4.3 |
| | Pharyngolaryngeal pain | 1 | 2 | 1 | 2 | 1 | 7 | 14.9 |
| Skin and subcutaneous tissue disorders | Rash generalised | | | | | 1 | 1 | 2.1 |

Transient redness and swelling was observed at the site of administration in some subjects, with redness affecting all subjects in cohorts 3 and 4. Although the incidence of injection site reactions appears to be increased in higher dose groups it is believed that this is related to the increased volume (and number) of injections.

Forty-eight (48) treatment emergent adverse events were reported in the seven weeks following dosing. The majority of these (44 events, 91.7%) were mild, with the remainder being moderate (4 events, 8.3%). There were no severe adverse events and no serious adverse events during this period. There was no apparent relationship between the doses of TACI-Fc5 administered and the incidence, intensity or assigned relationship of adverse events. The adverse events reported to date are summarized in Table 3.

A non-compartmental analysis of TACI serum concentrations was performed. This preliminary analysis was performed using nominal sampling times. Subjects 2, 6 and 13 had measurable concentrations pre-dose, thus baseline concentrations were subtracted from all post-dose measurements prior to analysis. Pharmacokinetic parameters following single subcutaneous doses of 2.1, 70, 210 and 630 mg are summarized in Table 4. Drug concentrations were close to the limit of quantitation of the assay following the 2.1 mg dose of TACI-Fc5, limiting the value of the data at this dose level. At doses of 70 mg and above, $T_{max}$ (time to maximal absorption) ranged from 16 to 36 hours and the overall median $t_{1/2}$ (calculated from the terminal portion of the curve) was 303 hours. In addition, the AUC (extrapolated to infinity) and the $C_{max}$ increased in a greater than dose proportional manner.

TABLE 4

PK parameters

| Parameter | Treatment | n | | | Min | Median | Max | CV |
|---|---|---|---|---|---|---|---|---|
| Cmax (μg/mL) | 2.1 mg | 5 | 0.015 | 0.011 | 0.005 | 0.013 | 0.032 | 74 |
| Tmax (h) | 2.1 mg | 5 | — | — | 8 | 72 | 336 | — |
| t½ (h) | 2.1 mg | 4 | 204 | 180 | 45 | 203 | 365 | 88 |
| AUC (h·μg/mL) | 2.1 mg | 4 | 8.55 | 9.65 | 0.524 | 6.62 | 20.4 | 113 |
| % AUC extrap | 2.1 mg | 4 | 36 | 24 | 13 | 32 | 69 | 65 |
| CL/F (L/h) | 2.1 mg | 4 | 1.70 | 1.90 | 0.10 | 1.34 | 4.01 | 112 |
| Cmax (μg/mL) | 70 mg | 5 | 0.617 | 0.236 | 0.426 | 0.496 | 0.985 | 38 |
| Tmax (h) | 70 mg | 5 | — | — | 16 | 16 | 36 | — |
| t½ (h) | 70 mg | 5 | 255 | 23 | 219 | 264 | 276 | 9 |
| AUC (h·μg/mL) | 70 mg | 5 | 79.7 | 15.7 | 65.4 | 72.5 | 101 | 20 |
| % AUC extrap | 70 mg | 5 | 10 | 1 | 9 | 11 | 11 | 12 |
| CL/F (L/h) | 70 | 5 | 0.90 | 0.17 | 0.69 | 0.97 | 1.07 | 18 |
| Cmax (μg/mL) | 210 mg | 5 | 3 | 0.902 | 1.84 | 2.90 | 4.16 | 30 |
| Tmax (h) | 210 mg | 5 | — | — | 12 | 16 | 36 | — |
| t½ (h) | 210 mg | 5 | 429 | 160 | 169 | 433 | 568 | 37 |
| AUC (h·μg/mL) | 210 mg | 5 | 260 | 72 | 167 | 267 | 344 | 28 |
| % AUC extrap | 210 mg | 5 | 6 | 3 | 1 | 6 | 9 | 54 |
| CL/F (L&L) | 210 mg | 5 | 0.86 | 0.26 | 0.61 | 0.79 | 1.25 | 31 |
| Cmax (μg/mL) | 630 mg | 4 | 13.9 | 2.79 | 11.4 | 13.7 | 16.7 | 20 |
| Tmax (h) | 630 mg | 4 | — | — | 16 | 16 | 16 | — |
| t½ (h) | 630 mg | 4 | 313 | 16 | 291 | 316 | 329 | 5 |
| AUC (h·μg/mL) | 630 mg | 4 | 992 | 194 | 719 | 1040 | 1170 | 20 |
| % AUC extrap | 630 mg | 4 | 2 | 0 | 1 | 2 | 2 | 18 |
| CL/F (L/h) | 630 mg | 4 | 0.66 | 0.15 | 0.54 | 0.61 | 0.88 | 23 |

Pharmacodynamic analyses have shown reductions in baseline IgM levels in the seven weeks following single doses of 70, 210 or 630 mg. Although no clear dose response relationship could be established with the small sample size, the extent of the IgM reduction was greatest in the highest dose group. Subjects in the 70 mg dose group appeared to show a return of IgM levels towards baseline by seven weeks post dose. Levels in the higher dose groups remained suppressed at this time point. There were no apparent effects upon IgG levels, or upon the lymphocyte subpopulations that were measured by FACS.

There was increase in levels of BLyS/TACI-Fc5 complexes proportionately during the sampling period, reaching a plateau by approximately 600 hours post dose. Conclusion: human data obtained in healthy male volunteers have shown TACI-Fc5 is safe and well tolerated by subjects at doses up to 630 mg. The nature, incidence and severity of adverse events were comparable between TACI-Fc5 treatment groups and placebo. There were no clinically significant changes in physical examination findings, vital signs, 12-lead ECGs or in safety laboratory parameters. Local tolerability at the site of administration was good. These data support the proposed doses in subjects with BCM.

After single doses in healthy male subjects, TACI-Fc5 reached $T_{max}$ between 16 and 20 hours AUC increased in a dose-proportional manner, though increases in $C_{max}$ were greater than dose proportional. Median half-life of TACI-Fc5 was approximately 300 hours. A pharmacodynamic effect was noted upon IgM levels at doses of 70, 210 and 630 mg. There was no apparent effect of treatment upon IgG or lymphocyte subpopulations following a single dose of TACI-Fc5.

There are no known or anticipated risks of particular severity or seriousness that have not already been taken into account in the proposed study protocols.

Example 3

Treating Non-Hodgkin's Lymphoma Patients with TACI-Fc5 Compositions

Patients are clinically assessed prior to weekly administration of TACI-Fc5. For consistency, TACI-Fc5 is targeted to be administered at approximately the same time (+/−6 hours) for each patient for each subsequent dose in the 5 week treatment period. Baseline assessments are defined as those assessments conducted immediately prior to the first administration of TACI-Fc5. The first day of TACI-Fc5 administration is designated as "Day 1". The following procedures are completed before administering to a patient the first dose of TACI-Fc5 medication: interval history, interval physical examination, VS, height and weight (first dose only), safety laboratory tests: hematology, coagulation, immunoglobulins and chemistry, assessment of concomitant medications/procedures, blood samples (timing recorded in e-CRF) for: PK measurement of TACI-Fc5 serum concentration, serum levels of free APRIL and BlyS, BLyS/TACI-Fc5 complex, cell counts by flow cytometry and measurement of anti TACI antibodies (first dose only).

Patients are administered subcutaneously from 2 mg/1 kg to 10 mg/1 kg of TACI-Fc5 formulation on day 1, 7, 14, 21 and 28.

The following post-dose assessments are completed: vital signs (for the subjects first dose of TACI-Fc5, VS will be taken at 1, 2, 4 and 8 hours post administration). Vital signs for subsequent doses of TACI-Fc5 are taken at 1 and 2 hours post administration; continuous assessment of adverse events; and continuous assessment of concomitant medications/procedures.

Special PK/PD assessments are completed on days 2, 3, and 4. These assessments include blood draws, PK measurements of TACI-Fc5 serum concentration, PD measurements of free APRIL and BlyS, BlyS/TACI-Fc5 complex, lymphocyte cell count and IgG and IgM serum concentration.

After all doses of TACI-Fc5 have been delivered, patients are evaluated weekly for an additional 4 weeks after their last dose of TACI-Fc5: continuous assessment of adverse events; continuous assessment of concomitant medications/procedures; interval history; interval physical examination, vital signs, safety laboratory tests: hematology, coagulation, immunoglobulins and chemistry, blood samples (timing recorded in e-CRF) for: PK measurement of TACI-Fc5 serum concentration, serum levels of free APRIL and BlyS, BLyS/TACI-Fc5 complex and cell counts by flow cytometry.

On the day 56 follow up visit, the following should be added to the above assessments: ECOG (Eastern Cooperative Oncology Group) score, height and weight, urinalysis, measurement of anti TACI antibodies. Anti-TACI antibodies are collected on day 85 for patients not entering the extension study.

Disease specific restaging is performed in conjunction with the final visit approximately 28 days after the final TACI-Fc5 treatment. Patients without disease progression at the time of restaging may entry into an extension treatment. Thoracic, abdominal, and pelvic CT and PET scans are recommended even if those areas were not initially involved because of the unpredictable pattern of recurrence in B-cell neoplasms. Bone marrow aspirate and biopsy if marrow involved with disease at enrollment. Tumor specific indicators of disease burden (e.g. frequency of the t (Mariette X., Ann Rheum Dis 2003; 62(2):168-171. Kelly et al. Cancer Res 2001; 60(4):1021-1027.) translocation by fluorescent in-situ hybridization in mantle cell lymphoma).

Patients who demonstrate recovery of both lymphocyte and immunoglobulin classes to either pretreatment baseline levels or absolute lymphocyte count >800/mm3, IgG >400 mg/dL, IgA >65 mg/dL and IgM >40 mg/dL are formally off study once they complete the 28 day safety follow-up after the final dose of TACI-Fc5. Patients who fail to meet these levels, complete blood counts and IgG, IgA and IgM levels assessed monthly until recovery is documented as defined above.

Example 4

TACI-Fc5 Injection Procedure

If subcutaneous route of administration is chosen for delivering TACI-Fc5, then the molecule is injected subcutaneously into the abdominal wall and sites rotated per the diagram below (FIG. 2). Care is taken not to inject into a blood vessel. It is extremely important to rotate sites to keep the skin healthy. Repeated injections in the same spot can cause scarring and hardening of fatty tissue. The following areas should be used for injection and rotated by week as follows (FIG. 2): injection into right upper external area during week 1; injection into left lower external area during week two; injection into right lower external area during week three; injection into left upper external area during week four and injection into median lower area during week five.

For patients requiring more than one injection per dose, injection begins at the twelve o'clock position for the site area designated to be injected for that week (as per FIG. 2, weeks 1-5) and then rotated sequentially clockwise, 2 hours, 4 hours, 6 hours, 8 hours and/or the 10 hour position as needed for the required number of injections per dose. Injections need to be at least 2.5 cm (1 inch) apart from each other and injected as close as possible in time. No injection of more than 1.5 mL into one injection site is allowed. If a patient experiences difficulty with injections into the abdomen, alternate areas that may be injected are: areas 6 & 7 (anterior thighs, FIG. 2); and areas 8 & 9: (upper arms, FIG. 2).

Common symptoms of site of injection reactions include itching, tenderness, warmth, and/or redness at the site of the injection.

Example 5

Dose Escalation Protocol for Administering TACI-Ig Molecule

This dose escalation protocol for evaluation of TACI in B cell malignancies (BCM) allows for dosing of two patients in a given dose cohort (2 mg/kg, 4 mg/kg, 7 mg/kg, 10 mg/kg) weekly for five weeks, followed by 8 days of observation. Provided that no Dose Limiting Toxicity (DLT) is observed, one additional patient can be treated at the current dose level. After the third patient has received the specified dose for five consecutive weeks and observed for two weeks, and provided that no DLT is observed, escalation may occur and two patients can be treated at the next sequential dose level. An additional two patients may be concurrently treated at the previous dose level, at which no DLT was observed, escalation may occur (FIG. 1). This conservative dose escalation scheme was based upon the limited pre-clinical and clinical experience with TACI-Fc5 prior to initiation of the BCM study.

Three patients have been enrolled and treated in the dose escalation study in BCM to date at a dosage of 2 mg/kg, and 2 patients are currently enrolled and being treated in the 4 mg/kg dosing cohort.

A total of 118 patients have been treated to date with either a single or a repeat dose regimen of TACI-Fc5 or placebo (92 active drug, 26 placebo) in the four ongoing studies. Each of the studies is performed under the auspices of a Safety Review Board or a Safety Monitoring Committee.

The SRB/SMC for these studies have performed a total of nine reviews, from cohorts of patients receiving single and repeated subcutaneous doses of TACI-Fc5 up to a cumulative dose of 60 mg/kg (three cycles of 5 weeks treatment and a 4-week washout period). No concerns have been raised by these committees with respect to safety of TACI-Fc5 treatment. In addition, continuous safety surveillance has not identified any clinically relevant safety issues to date.

In the TACI-Fc5 multiple myeloma trial, a total of 6 patients in Cohorts 1 and 2 have completed the dose escalation trial, in which they have received injections of 2 mg/kg (3 patients) or 4 mg/kg (3 patients) weekly for five weeks, followed by four weeks of observation. In addition, three patients in Cohort 3 have been dosed at 7 mg/kg weekly for one week. Two patients from Cohort 1 and one patient from Cohort 2 achieved stable disease in the dose-escalation study and have been entered into the extension trial.

Each of these patients has received up to 10 additional weekly injections of 2 mg/kg or 4 mg/kg. The doses selected for the evaluation of TACI-Fc5 in BCM are the same as those in the above described multiple myeloma trial: 2, 4, 7 and 10 mg/kg administered in 5 weekly injections for a total cumulative dose of 10, 20, 35 and 50 mg/kg.

Exposure-based safety margins were calculated based on observed exposures in healthy volunteers receiving single doses of TACI-Fc5, predicted exposures in BCM patients and comparison to observed exposures in cynomolgus monkeys receiving 80 mg/kg every three days for four weeks (the NOAEL dose). Calculated safety margins for the starting dose of 2 mg/kg and the top proposed dose of 10 mg/kg are 291-fold and 46-fold, respectively.

TACI-Fc5, delivered to monkeys at doses of 0, 4, 2 and 10 mg/kg every third day for thirteen or thirty nine weeks did not induce signs of toxicity. Reductions in mature and total circulating B-cells, and a tendency toward reduction in immature B-cells, as well as a reduction in serum IgG and IgM, as well as depletion of B-cell competent areas of the spleen and lymph nodes were considered to be due to the pharmacodynamic activity of TACI-Fc5 and showed reversibility in animals subjected to recovery after thirteen weeks of treatment.

TACI-Fc5 delivered at the same doses to mice every other day for thirteen or twenty six weeks induced mainly time- and dose-related modifications associated with the expected pharmacological action of TACI-Fc5, including reductions in serum IgG and IgM and total and mature B-cells at all doses, accompanied by a trend toward decreases in serum gamma-globulins at all doses. Histology showed no toxicologically relevant changes, except for expected finding based on previous studies, including a decrease in B-cells in the cortex of the lymph nodes and the marginal zone of the spleen, and an increase in sub-acute inflammation at the injection site.

Given the current human and pre-clinical safety data, and particularly because the study agent has been well tolerated by subjects with multiple myeloma at 2, 4, and 7 mg/kg dosing levels for up to 15 doses over five months, concurrent enrolment of three subjects per dosing cohort is planned for the doses of 7 and 10 mg/kg.

Example 6

Further Treatment of Patients with Initial Beneficial Response to TACI-Fc5

Non-Hodgkin's lymphoma patients who responded positively to initial five weekly treatments with TACI-Fc5, are further treated with a weekly dose of TACI-Fc5. The patients receive up to twenty four consecutive weekly doses of TACI-Fc5, subcutaneously (SC) given in multiple injections, as necessary, of no more than 1.5 mL each. The liquid formulation of TACI-Fc5 is provided in vials with a concentration of 70 mg/0.5 mL for each injection.

These additional twenty four consecutive injections are given at the same dose level that patients previously tolerated in the initial five-week treatment. However, patients who initially received 10 mg/kg of TACI-Fc5, may receive a scaled-down dose of 7 mg/kg.

What is claimed is:

1. A method for treatment of non-Hodgkin's lymphoma in a patient in need of such treatment comprising administering to the patient a composition comprising a fusion molecule selected from the group consisting of:
   1) a fusion molecule comprising: (i) TACI extracellular domain wherein said TACI extracellular domain consists of the sequence of SEQ ID NO: 1, and (ii) a human immunoglobulin-constant domain;
   2) a fusion molecule comprising amino acids 30-110 of SEQ ID NO: 1 and a human immunoglobulin-constant domain;
   3) a fusion molecule consisting of amino acids 30-110 of SEQ ID NO: 1 and a human immunoglobulin-constant domain; and
   4) a fusion molecule consisting of amino acids 30-110 of SEQ ID NO: 1 and the human immunoglobulin-constant domain of SEQ ID NO:2;

wherein said composition is administered in an amount from 0.01 mg per 1 kg of patient's body weight to 10 mg per 1 kg of patient's body weight and wherein said composition is administered 5 times during a 4-week interval followed by administration of the composition on a weekly basis at least during 2 more additional weeks, and wherein said composition is administered subcutaneously or intravenously.

2. The method of claim 1, wherein said composition is administered in said amount once a week during 2 to 30 weeks.

3. The method of claim 1, wherein said method further comprises administering a medicament.

4. The method of claim 3, wherein said medicament is selected from the group consisting of bisphosphonate, erythropoietin, granulocyte growth factors, granulocyte colony stimulating factor, drugs for the management of pain, melphalan, vincristine, doxorubicin, thalidomide and nucleoside analogs.

5. The method of claim 1 in which the patient is a human.

6. The method of claim 1, wherein said human immunoglobulin-constant domain is a human immunoglobulin-constant domain of IgG.

7. The method of claim 6, wherein said human immunoglobulin-constant domain comprises Fc5.

8. A method for treatment of non-Hodgkin's lymphoma in a patient in need of such treatment comprising administering to the patient a composition comprising a fusion molecule selected from the group consisting of:
   1) a fusion molecule comprising amino acids 30-110 of SEQ ID NO: 1 and a human immunoglobulin-constant domain;
   2) a fusion molecule consisting of amino acids 30-110 of SEQ ID NO: 1 and a human immunoglobulin-constant domain; and
   3) a fusion molecule consisting of amino acids 30-110 of SEQ ID NO: 1 and the human immunoglobulin-constant domain of SEQ ID NO:2;

wherein said composition is administered in an amount from 0.01 mg per 1 kg of patient's body weight to 10 mg per 1 kg of patient's body weight and wherein said composition is administered 5 times during a 4-week interval followed by administration of the composition on a weekly basis at least during 2 more additional weeks, and wherein said composition is administered in route other than oral subcutaneously or intravenously.

9. The method of claim 8, wherein said method further comprises administering a medicament.

10. The method of claim 9, wherein said medicament is selected from the group consisting of bisphosphonate, erythropoietin, granulocyte growth factors, granulocyte colony stimulating factor, drugs for the management of pain, melphalan, vincristine, doxorubicin, thalidomide and nucleoside analogs.

11. The method of claim 8, wherein the patient is a human.

12. The method of claim 8, wherein said human immunoglobulin-constant domain is a human immunoglobulin-constant domain of IgG.

13. The method of claim 12, wherein said human immunoglobulin-constant domain comprises Fc5.

14. The method of claim 8, wherein said composition is administered in said amount once a week during 2 to 30 weeks.

15. The method of claim 14, wherein said method further comprises administering a medicament.

16. The method of claim 15, wherein said medicament is selected from the group consisting of bisphosphonate, erythropoietin, granulocyte growth factors, granulocyte colony stimulating factor, drugs for the management of pain, melphalan, vincristine, doxorubicin, thalidomide and nucleoside analogs.

17. The method of claim 14, wherein the patient is a human.

18. The method of claim 17, wherein said human immunoglobulin-constant domain is a human immunoglobulin-constant domain of IgG.

19. The method of claim 18, wherein said human immunoglobulin-constant domain comprises Fc5.

* * * * *